US009873613B2

(12) United States Patent
Toutonghi

(10) Patent No.: US 9,873,613 B2
(45) Date of Patent: Jan. 23, 2018

(54) NANO OR MACRO MATERIAL FUNCTIONALIZATION AND SELF ASSEMBLED CONSTRUCTION MEDIATED BY TRIS(TRIMETHYLSILYL)SILANE

(71) Applicant: FUNCTIONALIZE, INC., Seattle, WA (US)

(72) Inventor: Michael Toutonghi, Seattle, WA (US)

(73) Assignee: Functionalize, Inc., Seattle, WA (US)

( * ) Notice: Subject to any disclaimer, the term of this patent is extended or adjusted under 35 U.S.C. 154(b) by 0 days.

(21) Appl. No.: 15/121,722

(22) PCT Filed: Feb. 27, 2015

(86) PCT No.: PCT/US2015/018197
§ 371 (c)(1),
(2) Date: Aug. 25, 2016

(87) PCT Pub. No.: WO2015/131160
PCT Pub. Date: Sep. 3, 2015

(65) Prior Publication Data
US 2016/0376152 A1 Dec. 29, 2016

Related U.S. Application Data

(60) Provisional application No. 62/082,037, filed on Nov. 19, 2014, provisional application No. 61/946,029, filed on Feb. 28, 2014.

(51) Int. Cl.
*C08K 9/00* (2006.01)
*C01B 31/02* (2006.01)
(Continued)

(52) U.S. Cl.
CPC ...... *C01B 31/0253* (2013.01); *C01B 31/0266* (2013.01); *C01B 31/0273* (2013.01); *C07C 17/275* (2013.01); *C07C 319/02* (2013.01); *C07F 1/005* (2013.01); *C07F 5/069* (2013.01); *C07F 7/28* (2013.01); *C07F 11/005* (2013.01); *C07F 15/025* (2013.01);
(Continued)

(58) Field of Classification Search
None
See application file for complete search history.

(56) References Cited

U.S. PATENT DOCUMENTS 6,132,801 A 10/2000 Linford
2008/0093211 A1 4/2008 Ramanath et al.
(Continued)

FOREIGN PATENT DOCUMENTS

WO 2013/019476 A2 2/2013

OTHER PUBLICATIONS

Fukuyama et al. "Spurring Radical Reactions of Organic Halides with Tin Hydride and TTMSS Using Microreactors", Org. Lett. 2008, 10, 533-536.*
(Continued)

*Primary Examiner* — Robert S Loewe
(74) *Attorney, Agent, or Firm* — Seed Intellectual Property Law Group PLLC

(57) ABSTRACT

Disclosed herein are radically initiated process involving tris(trimethylsilyl)silane that are suitable for surface functionalization or formation of composite materials based on functionalized nanoparticles.

18 Claims, 8 Drawing Sheets

(51) Int. Cl.

| | | |
|---|---|---|
| C09C 1/56 | (2006.01) | |
| C08J 5/00 | (2006.01) | |
| C07C 17/275 | (2006.01) | |
| C07C 319/02 | (2006.01) | |
| C07F 1/00 | (2006.01) | |
| C07F 5/06 | (2006.01) | |
| C07F 7/28 | (2006.01) | |
| C07F 11/00 | (2006.01) | |
| C07F 15/02 | (2006.01) | |
| C08G 63/91 | (2006.01) | |
| C09C 1/44 | (2006.01) | |
| C09C 1/62 | (2006.01) | |
| C09C 1/64 | (2006.01) | |
| B82Y 30/00 | (2011.01) | |
| B82Y 40/00 | (2011.01) | |

(52) U.S. Cl.
CPC ............ *C08G 63/912* (2013.01); *C08J 5/005* (2013.01); *C08K 9/00* (2013.01); *C09C 1/44* (2013.01); *C09C 1/56* (2013.01); *C09C 1/62* (2013.01); *C09C 1/648* (2013.01); *B82Y 30/00* (2013.01); *B82Y 40/00* (2013.01); *C07C 2604/00* (2017.05); *C08J 2367/04* (2013.01); *Y10S 977/746* (2013.01); *Y10S 977/847* (2013.01)

(56) References Cited

U.S. PATENT DOCUMENTS

2009/0171459 A1\* 7/2009 Linhardt ................. A61L 27/34
623/6.56
2009/0311875 A1\* 12/2009 Rogojina ................ C01B 33/02
438/765

OTHER PUBLICATIONS

Postigo et al., "Radical Reactions in Aqueous Medium Using $Me_3Si)_3SiH$," *Organic Letters* 9(25):5159-5162, 2007.

Stewart et al., "Exciton-Mediated Hydrosilylation on Photoluminescent Nanocrystalline Silicon," *J. Am. Chem. Soc.* 123:7821-7830, 2001.

\* cited by examiner

NANO OR MACRO MATERIAL FUNCTIONALIZATION AND SELF ASSEMBLED CONSTRUCTION MEDIATED BY TRIS(TRIMETHYLSILYL)SILANE

CROSS-REFERENCES TO RELATED APPLICATIONS

This application claims the benefit under 35 U.S.C. §119(e) of U.S. Provisional Patent Application No. 61/946, 029, filed Feb. 28, 2014, and U.S. Provisional Patent Application No. 62/082,037, filed Nov. 19, 2014, which applications are incorporated herein by reference in their entirety.

BACKGROUND

Technical Field

The present disclosure relates to Nano-Composite Materials (NCMs), and methods of making or functionalizing the same. Specifically, the NCMs may include multiple types of nanoparticles combined together into a single composite material or the NCM may be a combination of nanoparticles and macro-scale substrates.

Description of the Related Art

Many nano-materials, including carbon nanotubes, graphene, buckyballs, carbyne, nano-diamonds, nanoparticles of titanium dioxide, silica, tungsten, magnetite, and other metal, semiconductor, and metal oxide nanoparticles, exhibit exceptional mechanical, thermal, optical, catalytic, magnetic, and/or electrical properties. Compositing two or more nanomaterials could potentially improve electrical, thermal, optical, mechanical, or chemical interfaces between said nanomaterials.

Numerous methods have been developed to attach, or "functionalize," specific chemical or functional groups to target materials, including nano-materials and macro-scale material surfaces. These chemical groups can then further bond or adsorb to additional chemicals, other nanoparticles, or provide anchors for attachment to macro scale surfaces in the form of self-assembled monolayers (SAMs) or self-assembled poly-layers (SAPs). In general, material-specific functionalization protocols are designed and employed in order to ensure the specificity or selectivity for attaching the chemical groups.

On the other hand, a few processes, including those that use thiols or reactive diazonium salts, can be widely applied to functionalizing materials such as all forms of carbon, numerous metals, and semiconductors.

For example, a common, material-specific functionalization process for graphitic carbon materials, such as carbon nanotubes, graphene, or buckyballs, employs strong oxidizing agents, such as a mixture of concentrated sulfuric acid and nitric acid. In addition, the process requires harsh sonication treatments that introduce defects onto the otherwise stable, relatively inert graphitic structure. The combination of oxidation and sonication is capable of forming a non-stoichiometric number of mixed chemical groups, such as hydroxyls, carboxyls, ketones, etc. Some of these chemical groups can then be used as anchors for further attachment of functional groups, to enhance solubility in certain solvents, or for other application-specific purposes.

Another example of functionalization is more general in its range of target materials and also more precise in its ability to stoichiometrically functionalize a substrate. The process involves treating a target material with an aryl diazonium salt, such as 4-carboxybenzenediazonium tetrafluoroborate, under conditions that facilitate electron transfer to the diazonium salt, thereby generating a transient aryl radical. The transient and reactive aryl radical then forms a carbon-substrate bond with the substrate. The reaction conditions required for diazonium functionalization are relatively mild, as are the facile formation of a direct carbon-substrate bond. Thus, diazonium functionalization is widely used for many materials, including silicon; gallium arsenide; copper; gold; palladium; zinc; zinc oxides; titanium; tungsten; ruthenium; platinum; iron; iron oxides; copper oxides; tungsten oxides; all carbon allotropes that have either graphitic structure, alkene or alkyne functional groups, or molecular defects; and many more nano-materials and substrates.

In fact, due to the broad range of substrates and the ability to form extremely strong carbon-substrate bonds with many materials, including carbon itself, diazonium functionalization is considered one of the more important reactions in nanomaterial science. However, because the diazonium functional group is so unstable that only aryl compounds will not spontaneously decompose, the molecules used to functionalize materials using diazonium are limited to functionalities which have an aryl ring between the functionalized nanomaterial or substrate and the desired functional groups attached. This limitation can often reduce atom efficiency, limit material properties, or prevent the use of less expensive precursors for a specific functionalization task. Accordingly, there is a need for a process that could functionalize a nanomaterial or macro-scale material surface by more versatile attachments and functional groups.

BRIEF SUMMARY

Disclosed herein is an alternative method of functionalization by creating a substrate-carbon bond through a radical approach mediated by tris(trimethylsilyl)silane (TTMSS). While the process disclosed herein is capable of using aryl compounds as precursors for functionalization, unlike the diazonium approach, it is not limited to only aryl radical precursors, thus allowing for a much broader range of functional groups. In addition, the disclosed process is compatible with functionalizing a broad range of substrates, including those that have been previously found difficult to functionalize by the diazonium approach.

One embodiment provides a process of functionalizing a substrate, comprising:

providing a substrate having a surface;

providing a reaction mixture by combining with the substrate (a) a functionalizing unit represented by Fn-$(X)_m$, wherein Fn is an organic moiety, X is, at each occurrence, the same or different and independently halogen, acyl halide, isocyanide, thionoester, xanthate, selenide, isocyanate, thiocyanate, sulfide, triflate, selenocyanide, or a Barton ester covalently connected to a respective carbon atom of Fn, and m is an integer $\geq 1$;

(b) tris(trimethylsilyl)silane; and (c) a radical initiator; and allowing the reaction mixture to react for a sufficient period of time to provide a surface-functionalized substrate comprising one or more Fn covalently attached to the surface of the substrate.

A further embodiment provides a premix TTMSS reaction precursor comprising:

(a) a functionalizing unit represented by Fn-$(X)_m$, wherein Fn is an organic moiety, X is, at each occurrence, the same or different and independently halogen, acyl halide, isocyanide, thionoester, xanthate, selenide, isocyanate, thiocyanate, sulfide, triflate, selenocyanide, or a Barton ester covalently connected to a respective carbon atom of Fn, and m is an integer ≥1; and (b) tris(trimethylsilyl)silane.

Yet another embodiment provides a process for forming a composite material, comprising:

providing a first substrate;

providing a first reaction mixture by combining with the first substrate:

(a) a functionalizing unit represented by Fn-(X)$_m$, wherein Fn is an organic moiety, X is, at each occurrence, the same or different and independently halogen, acyl halide, isocyanide, thionoester, xanthate, selenide, isocyanate, thiocyanate, sulfide, triflate, selenocyanide, or a Barton ester covalently connected to a respective carbon atom of Fn, and m is an integer ≥2;

(b) tris(trimethylsilyl)silane; and (c) a radical initiator; and allowing the first reaction mixture to react for a sufficient period of time to provide a functionalized first substrate comprising one or more Fn covalently attached to the surface of the first substrate, wherein at least one X group remains on the covalently attached Fn;

combining the functionalized first substrate with a second substrate with tris(trimethylsilyl)silane and a radical initiator to form a second reaction mixture; and allowing the second reaction mixture to react for a sufficient period of time to provide a functionalized second substrate covalently bonded to the first substrate via Fn.

Yet another embodiment provides process for forming a composite material, comprising:

providing a premix mixture of a first substrate and a second substrate;

providing a reaction mixture by combining the first and second substrates with:

(a) a functionalizing unit represented by Fn-(X)m, wherein Fn is an organic moiety, X is, at each occurrence, the same or different and independently halogen, acyl halide, isocyanide, thionoester, xanthate, selenide, isocyanate, thiocyanate, sulfide, triflate, selenocyanide, or a Barton ester covalently connected to a respective carbon atom of Fn, and m is an integer ≥2; and (b) tris(trimethylsilyl)silane; and exposing the reaction to a radical initiator for a sufficient period of time to form covalent bonds between the first and second substrates via Fn.

Another embodiment provides a functionalized nanomaterial comprising: a thermoplastic polymer; and a plurality of nanoparticles dispersed in the thermoplastic polymer and at least some of the nanoparticles are covalently coupled the thermoplastic polymer.

A further embodiment provides a nanocomposite material comprising: a first plurality of nanoparticles; a second plurality of nanoparticles; wherein the first plurality of nanoparticles are covalently bonded to the second plurality of nanoparticles via an organic moiety, wherein the organic moiety is alkyl, alkenyl, alkynyl, or a combination thereof, or a polymeric moiety.

Yet another embodiment provides a nanocomposite material comprising: a graphitic carbon substrate comprised of a plurality of conjugated carbon rings, each having 5, 6, or 7 carbon atoms; a plurality of metal nanoparticles; wherein the plurality of metal nanoparticles are covalently bonded to the carbon substrate via a carbon-metal, carboxylate-metal, amine-metal, xanthate-metal, or thiolate-metal functionalized organic moiety, which is further directly bonded to a carbon substrate within the inner carbons of the plurality of carbon rings, wherein the organic moiety is alkyl, alkenyl, alkynyl, or a combination thereof, and wherein the substrate carbon to which the moiety is bonded is further bonded directly to 3 other substrate carbons.

A further embodiment provides a nanocomposite material comprising: a graphitic carbon substrate comprised of a plurality of conjugated carbon rings, each having 5, 6, or 7 carbon atoms; a plurality of polymer molecules; wherein the plurality of polymer molecules are covalently bonded to an inner carbon of the substrate's plurality of carbon rings, the substrate via an organic moiety having a polymer-specific functional group, wherein the organic moiety is alkyl, alkenyl, alkynyl, or a combination thereof, and wherein the substrate carbon to which the moiety is bonded is further bonded directly to 3 other substrate carbons.

BRIEF DESCRIPTION OF THE DRAWINGS

The foregoing summary as well as the following detailed description of the preferred embodiment of the invention will be better understood when read in conjunction with the appended drawings. It should be understood, however, that the invention is not limited to the precise arrangements and instrumentalities shown herein. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

Figure 1:
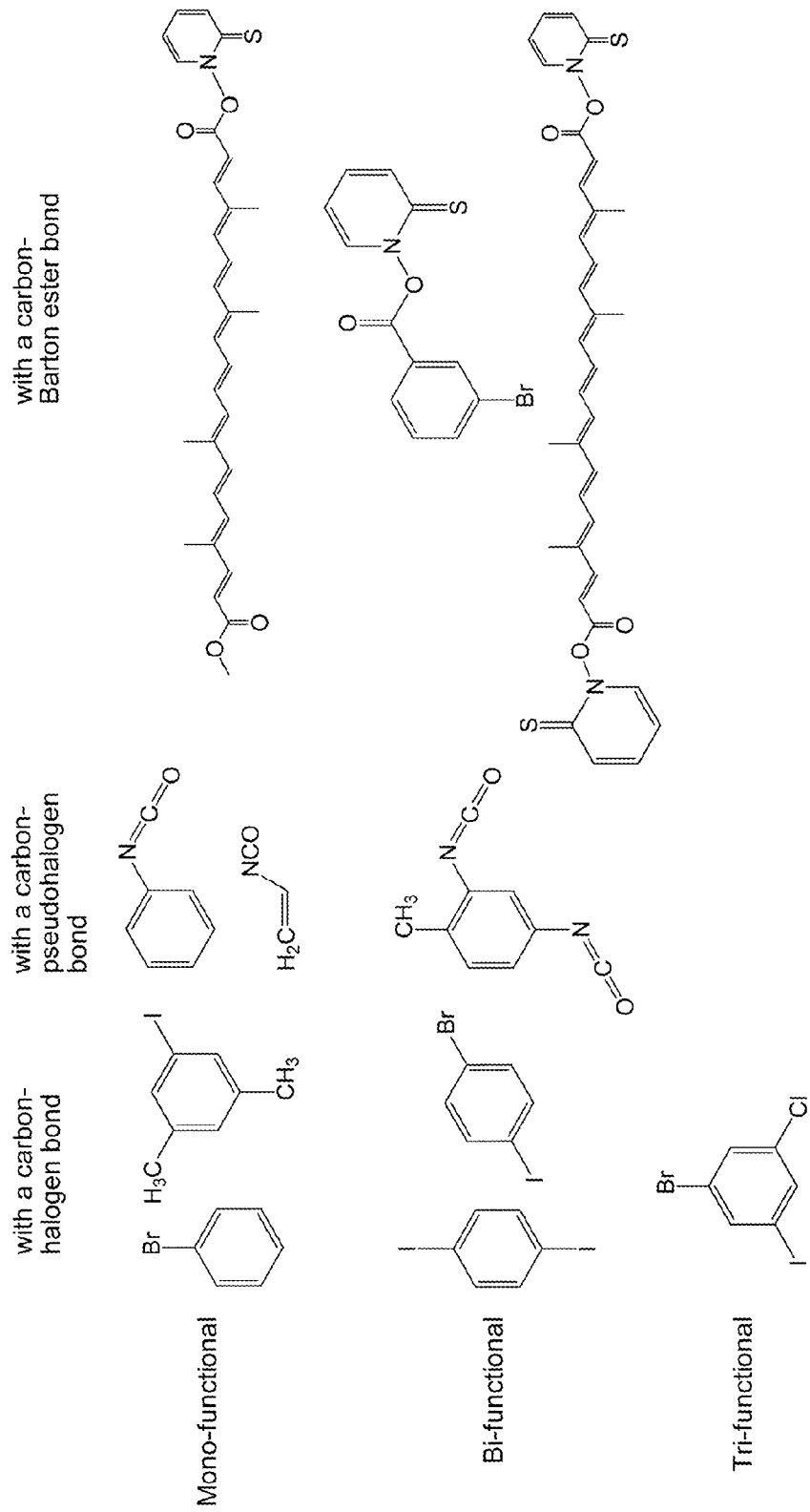
FIG. 1 shows the structures of representative "functionalizing units" in accordance with embodiments of the disclosure.

Generally, according to various embodiments, the process employs a system that includes tris(trimethylsilyl)silane (TTMSS), and a radical initiator, for facile functionalization of a substrate (including NCMs). A variety of organic molecules having one or more bonds formed between carbon and one of the following groups: halogen, acyl halide, isocyanide, thionoester, xanthate, selenide, isocyanate, thiocyanate, sulfide, triflate, selenocyanide, or a Barton ester, as well as other functional groups can be used to couple to the substrate by forming a carbon-substrate bond. Preferably, following the TTMSS-mediated coupling to the substrate, these organic molecules retain additional functional groups, which act as reactive sites for further reactions.

TTMSS is a non-toxic, environmentally friendly radical reducing agent. When employed with a radical initiator, e.g., molecular oxygen, a heat or photo-sensitive radical initiator, or a combination thereof, TTMSS is converted to a transient TTMSS radical:

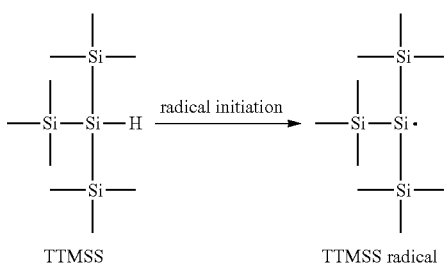

TTMSS → TTMSS radical (radical initiation)

The organic molecule to be coupled to the substrate typically contains at least a leaving group, such as a halogen, acyl halide, isocyanide, thionoester, xanthate, selenide, isocyanate, thiocyanate, sulfide, triflate, selenocyanide, or a Barton ester. The leaving group is reactive toward the TTMSS radical. Once the leaving group is removed, the remainder of the organic molecule is in the form of an organic radical, which can attach covalently to a variety of substrates (including nanoparticles and macro-scale material surface) under ambient conditions. The covalent attachment of the organic molecule thus "functionalizes" the substrate.

As used herein, an organic molecule that reacts with TTMSS and is ultimately coupled to a substrate is also referred to as a "functionalizing unit." The functionalizing unit comprises an organic moiety (Fn) and one or more leaving groups. The organic moiety is any carbon-based organic group and may be specifically an aryl, alkyl, alkenyl, alkynyl, cycloalkyl, cycloalkenyl, heterocyclyl heteroaryl, or a combination thereof, or a polymer, as defined herein. The one or more leaving groups are connected, through one or more covalent bonds, to one or more carbons of the organic moiety. The leaving groups may be the same or different and independently halogen, acyl halide, isocyanides, thionoester, xanthate, selenides (e.g., phenyl selenide), isocyanate, thiocyanate, sulfides (e.g., phenyl sulfide), triflates, and selenocyanides or Barton ester. In a TTMSS-mediated reaction, a homolytic fragmentation of the bond between the leaving group and the carbon to which it attaches produces a radical of the organic moiety (Fn), which is available for forming a direct bond with a substrate. In other words, the cleaved leaving groups are abstracted by the TTMSS radical. The functionalizing unit may also include, besides the leaving group, other functional groups, linker groups, functional group precursors, preferably those which will not react at a higher rate with TTMSS than the above leaving groups to be cleaved and further that will not react appreciably with the subsequently generated radical itself. The TTMSS-mediated functionalization is shown in the following reaction scheme. The functionalizing unit is indicated as Fn-X, in which Fn is an organic moiety and X is a leaving group:

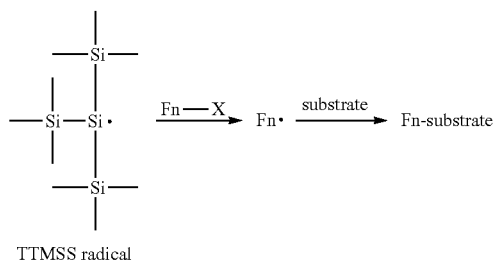

TTMSS radical

Advantageously, the process disclosed herein is capable of utilizing functionalizing units having multiple leaving groups as points for multiple covalent attachments to a single substrate, as shown above.

Alternatively, the functionalizing unit can carry multiple leaving groups to be used in sequential functionalizations of multiple substrates by using molar amounts of TTMSS to selectively activate leaving groups according to their reactivities. For instance, a TTMSS-mediated reaction may first only cleave the most reactive leaving groups of the functionalizing unit. Following a first step of functionalization of a first substrate, the functionalizing unit may be further activated, i.e., cleaved at a less reactive leaving group, in order to generate another radical. The sequential functionalization is easy to control and can proceed as the leaving groups are removed in a descending order of reactivities toward the TTMSS-mediated reaction. The following reaction scheme shows a sequential functionalization of a first substrate (S1) and a second substrate (S2) via the use of a bi-functional functionalizing unit having two leaving groups (X1 and X2):

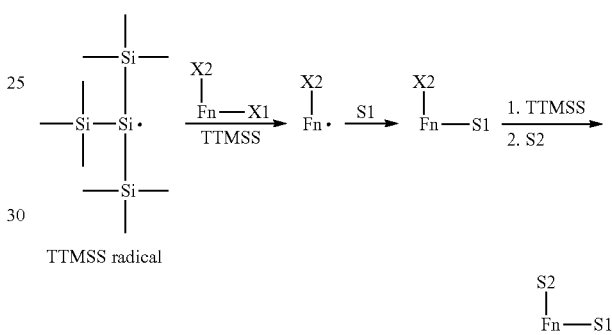

Such an advantage allows the use of a functionalizing units that are bi-, tri-, or otherwise multi-substituted with leaving groups as a multistep precursor for functionalization. Advantageously over a diazonium-based functionalization, which is limited to aryl precursors, the present invention is capable of employing aryl as well as most organic, halogenated precursors or molecules with tolerant functional groups, which include halogen, acyl halide, isocyanide, thionoester, xanthate, selenide, isocyanate, thiocyanate, sulfide, triflate, selenocyanide, or a Barton ester, as precursors to form carbon-substrate bonds. FIG. 1 shows the structures of representative "functionalizing units" in accordance with various embodiments of the disclosure.

Also advantageously over a diazoninum-based functionalization, which harbors dangerous explosive risks, the TTMSS-mediated process is mild and not prone to explosions.

Thus, one embodiment provides a process of functionalizing a substrate, comprising:
providing a substrate having a surface;
providing a reaction mixture by combining with the substrate:
(a) a functionalizing unit represented by Fn-(X)$_m$, wherein Fn is an organic moiety, X is, at each occurrence, the same or different and independently halogen, acyl halide, isocyanide, thionoester, xanthate, selenide, isocyanate, thiocyanate, sulfide, triflate, selenocyanide, or a Barton ester covalently connected to a respective carbon atom of Fn, and m is an integer ≥1;
(b) tris(trimethylsilyl)silane; and
(c) a radical initiator; and allowing the reaction mixture to react for a sufficient period of time to provide a surface-functionalized substrate comprising one or more Fn covalently attached to the surface of the substrate.

Substrate

"Substrate" refers to any material that is to be functionalized via the formation of one or more carbon-substrate covalent bonds by a functionalizing unit in a TTMSS-mediated reaction. In some embodiments, the substrate may also be referred to as a "target material," which is to be functionalized or coupled to another substrate. In various embodiments, the substrate may be a nano-scale, micro-scale, or a macro-scale material.

In preferred embodiments, the substrate is a nano-scale material and comprises one or more nanoparticles. As used herein, nanoparticles are particles having at least one dimension in the nanometer range (i.e., less than 1 micron). The substrate may also be a micro-scale material that comprises one or more microparticles. Microparticles are particles in which the smallest dimension is in the micrometer range (i.e., 1 micron to less than 1 millimeter). The nanoparticles or microparticles can be sphere or elongated (e.g., in the shapes of wires, tubes, or rods). Examples of nano- or micro-scale substrates include, without limitation, carbon nanotubes, nanoparticles or microparticles of graphene, buckyballs, carbyne, nano-diamonds, nanoparticles or microparticles titanium dioxide, silica, magnetite, metal nanoparticles or microparticles, semiconductor nanoparticles or microparticles, and metal oxide nanoparticles or microparticles.

In certain embodiments, the substrate may include a combination of nanoparticles and microparticles.

In various embodiments, the substrate may be a macro-scale material. The macro-scale substrate may be the whole or a portion of a device, an apparatus or any objects in which the smallest dimension is at least 1 millimeter. The substrate may be metallic, metal oxide, semiconductive, polymeric, dielectric material, the surface of which may be functionalized. More specific examples of macro-scale substrates include, without limitation, silicon, graphene, polymers, metal-plated surfaces, or complex fluids.

Functionalization Unit

A functionalizing unit is a reactant that, under a TTMSS-mediated reaction, functionalizes the substrate. The functionalizing unit comprises an organic moiety (Fn) covalently bonded to one or more leaving groups, and is represented by Fn-$(X)_m$. In a TTMSS-mediated reaction, the leaving group is abstracted by the TTMSS radical to give rise to an Fn radical, which can be covalently bonded to the substrate.

1. Organic Moiety (Fn)

Fn is thus any organic moiety, that could be equipped with a leaving group in order to participate in the functionalization process. The Fn moiety is ultimately coupled to the substrate.

In some embodiments, the Fn moiety is aryl, alkyl, alkenyl, alkynyl, cycloalkyl, cycloalkenyl, heterocyclyl, or heteroaryl. It should be understood that although conventionally, "-yl" symbolizes a single attachment to another moiety. However, as used herein, an organic moiety having "-yl" symbol may have one or more attachments because the functionalizing unit may have multiple leaving groups, thus making multiple attachments possible. Thus, the aryl, alkyl, alkenyl, alkynyl, cycloalkyl, cycloalkenyl, heterocyclyl and heteroaryl moieties, as used herein, may have one or more attachments to another moiety, substrate, particles, and the like. Besides the leaving groups, any of these organic moieties may be substituted by one or more substituents, as defined herein.

"Aryl" refers to aromatic monocyclic or poly-cyclic hydrocarbon ring system, when unsubstituted, consisting only of hydrogen and carbon and containing from 6 to 30 carbon atoms, where the ring system may be partially or fully saturated, fused or bridged. Aryl groups include, but are not limited to groups such as fluorenyl, phenyl and naphthyl. Aryl also includes polycyclic aromatic hydrocarbons (PAH), such as phenanthrene, pyrene, coronene and the like. Besides the leaving groups, the aryl moiety may be substituted by one or more substituents, as defined herein.

"Alkyl" refers to a straight or branched hydrocarbon chain radical, when unsubstituted, consisting solely of carbon and hydrogen atoms, containing no unsaturation, having from one to twenty carbon atoms, preferably one to twelve, and preferably one to eight carbon atoms or one to six carbon atoms. Examples include methyl, ethyl, n-propyl, 1-methylethyl (iso-propyl), n-butyl, n-pentyl, 1,1-dimethylethyl (t-butyl), and the like. Besides the leaving groups, the alkyl moiety may be substituted by one or more substituents, as defined herein.

"Alkenyl" refers to a straight or branched hydrocarbon chain radical group, when unsubstituted, consisting solely of carbon and hydrogen atoms, containing at least one double bond. Alkenyl includes polyenes that may have up to 60-100 carbons, although polyenes or alkene are not limited to any number of carbons.

"Alkynyl" refers to a straight or branched hydrocarbon chain radical group, when unsubstituted, consisting solely of carbon and hydrogen atoms, containing at least one triple bond. Alkynyl may further comprise one or more double bonds.

"Cycloalkyl" refers to a stable non-aromatic monocyclic or bicyclic hydrocarbon radical, when unsubstituted, consisting solely of carbon and hydrogen atoms, having from three to fifteen carbon atoms, preferably having from three to twelve carbon atoms, and which contains no double bond in the ring structure.

"Cycloalkenyl" refers to a stable non-aromatic monocyclic or bicyclic hydrocarbon radical, when unsubstituted, consisting solely of carbon and hydrogen atoms, having from three to fifteen carbon atoms, preferably having from three to twelve carbon atoms, and which contains at least one double bond in the ring structure.

"Heterocyclyl" refers to a stable 3- to 18-membered non-aromatic ring radical including, as ring atoms, at least one carbon atom and from one to five heteroatoms selected from the group consisting of nitrogen, oxygen and sulfur. For purposes of this disclosure, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; and the nitrogen atom may be optionally quaternized; and the heterocyclyl radical may be partially or fully saturated.

"Heteroaryl" refers to an aromatic ring radical including, as ring atoms, at least one carbon atom and from one to five heteroatoms selected from the group consisting of nitrogen, oxygen and sulfur. For purposes of this disclosure, the heteroaryl radical may be a monocyclic or polycyclic ring system, which may include fused or bridged ring systems; and the nitrogen, carbon or sulfur atoms in the heteroaryl radical may be optionally oxidized; and the nitrogen atom may be optionally quaternized.

"Substituent" refers to amino, thiol, alkyl, aryl, haloalkyl, cyano, nitro, and the like.

In other embodiments, the Fn moiety may be a combination of two or more moieties selected from aryl, alkyl, alkenyl, alkynyl, cycloalkyl, cycloalkenyl, heterocyclyl, and heteroaryl. These discrete moieties can be connected by any covalent bonds, such as single bond (C—C), double bond (C=C), amide bond (—C(O)—NH—), ester bond (—C(O)—O—), thioester bond (—C(O)—S—), ether bond (—O—), thioether bond (—S—), carbamate bond (—NH—C(O)—O—), carbonate bond (—O—C(O)—O—), and the like.

In some embodiments, the Fn moiety comprises a polymer chain. A polymer typically has a linear structure of at least 10 repeating monomers. One or both terminal groups, or a side chain of the polymer can be further functionalized or coupled to a leaving group. The polymer may be thermoplastic polymer, such as polyamides (e.g., Nylon), polyacrylic acids, acrylates, polycarbonates, and the like. There is no particular limit on the molecular weight of the polymer. In some embodiments, the molecular weight is in the range of 300-200,000.

2. Leaving Group (X)

A leaving group is the reactive moiety in the functionalizing unit that is susceptible to the TTMSS-mediated reaction. The leaving group (X) is covalently coupled to a carbon atom of the remainder of the functionalizing unit (Fn). As the C—X bond is cleaved in the presence of the TTMSS radical, a radical of the Fn moiety is formed.

In various embodiments, X is a halogen, which may be iodo, bromo, or chloro group, in descending order of reactivities toward TTMSS radical. Other leaving group include isocyanides, thionoester, xanthate, selenides (e.g., phenyl selenide), isocyanate, thiocyanate, sulfides (e.g., phenyl sulfide), triflates, and selenocyanides. In yet another embodiment, the leaving group may be a Barton ester, e.g., thiohydroxamate ester. In further embodiment, the leading group may be an acyl halide, including acyl chloride, acyl bromide or acyl iodide.

3. Fn-$(X)_m$

As discussed herein, the functionalizing unit may contain one or more leaving groups ($m \geq 1$), enabling multiple points of attachment from the same functionalizing unit.

In various embodiments, the functionalizing unit may be 3-chloro-1-iodopropane, 2-bromo-chloroethane, 1-bromoproanoic acid, 1,4-diiodo-2,5-dimethylbenzene, 1,4-dibromo-2,5-dimethylbenzene, 1-bromo-2,6-dimethyl-4-iodobenzene, 1-bromo-2,5-dimethyl-iodobenzene. 1,4-diiodo-2,3,5,6-tetramethylbenzene, 1,4-dibromo-2,3,5,6-tetramethylbenzene, 3,5-diiodo-1-chlorobenzene, 1,3-dibromo-5-chlorobenzene, 1,3-diiodo-5-fluorobenzene, 1,3-dibromo-5-fluorobenzene, 1,4-diiodotetrachlorobenzene, 1,4-dibromotetrachlorobenzene, 1,4-diiodotetrafluorobenzene, and 1,4-dibromotetrafluorobenzene. See also FIG. 1.

In other embodiments, the functionalizing unit is derived from a polymer. An example of a polymeric functionalizing unit comprises a polylactic acid (PLA) chain. PLA has a hydroxy terminal and a carboxylic acid terminal. It can be initially functionalized by a bifunctional molecule such as a bromo-substituted carboxyl chloride (e.g., 4-bromobutyryl chloride). The bifunctional molecule is coupled, via the carboxyl chloride moiety, to the hydroxy terminal of the PLA. The PLA is thus functionalized with a halogen leaving group (e.g., bromo) at the terminus of the polymer chain. See also FIG. 2A.

Radical Initiator

The TTMSS reaction is initiated by a radical initiator and the TTMSS radical generated in situ proceeds to generate a radical of Fn, which forms a covalent bond with the substrate. A radical initiator is a substance that can produce radical species, usually under mild conditions (heat and/or light), the radical species further induces or promotes radical reaction, i.e., to generate a TTMSS radical.

Any radical initiator may be employed, including organic radical initiators such as azo and peroxide compounds. In addition to the common radical initiators, TTMSS is advantageously capable of mediating radical reactions which are initiated by molecular oxygen. Examples of organic radical initiators include, without limitation, an azobis initiator such as azobisisobutyronitrile (AIBN), 1,1'-Azobis(cyclohexanecarbonitrile) (ABCN), and water-soluble azobis-initiators, which are commercially available from, e.g., Wake Pure Chemical Industries, Ltd. Peroxide-based initiators include, for example, di-tert-butyl peroxide, benzoyl peroxide and methyl ethyl ketone peroxide. Advantageously, the TTMSS-mediated radical reaction can be initiated by molecular oxygen at ambient temperature.

In certain embodiments, the reaction mixture may further comprise one or more solvents, including, an aqueous-based solvent system such as water and dioxane. A variety of other hydrocarbon solvents may also be used as long as they are generally non-reactive towards TTMSS or the TTMSS radical as well as having a relatively low rate constant when reacting with the radical intermediate used for functionalization.

In other embodiments, the reaction mixture may proceed without a solvent, because TTMSS and certain halogen-based functionalizing units (e.g., chloro-iodopropane, halogenated benzene) are liquid at room temperature.

A further embodiment provides a premix TTMSS reaction precursor comprising:

(a) a functionalizing unit represented by Fn-$(X)_m$, wherein Fn is an organic moiety, X is, at each occurrence, the same or different and independently halogen, acyl halide, isocyanide, thionoester, xanthate, selenide, isocyanate, thiocyanate, sulfide, triflate, selenocyanide, or a Barton ester covalently connected to a respective carbon atom of Fn, and m is an integer $\geq 1$; and (b) tris(trimethylsilyl)silane.

The premix TTMSS reaction precursor provides a stable mixture of all the functionalizing components, except for the radical initiator. The reaction precursor should be prepared and stored in an oxygen-free environment and may be activated by adding a radical initiator (including molecular oxygen) immediately prior to a functionalization reaction.

Advantageously, certain specific functionalization gives rise to superior properties in the functionalized nanoparticles, in addition to retaining the original properties of the nanoparticles. For instance, due to the large surface/volume ratio and van der waals interactions, nanoparticles tend to aggregate. According to embodiments disclosed herein, functionalized nanoparticles may spontaneously disperse as covalent bonds are being formed with the functionalizing unit. The much stronger covalent bonding is believed to overcome the van der waals interactions between the nanoparticles, thereby causing disaggregation.

Carbon nanotubes or CNTs (single wall or multi-wall) are linear nanoparticles that have a strong tendency to aggregate. According to an embodiment of the present disclosure, polymer-functionalized carbon nanotubes can spontaneously disperse while retaining the electrical conductivity of the CNTs.

Figure 2A:
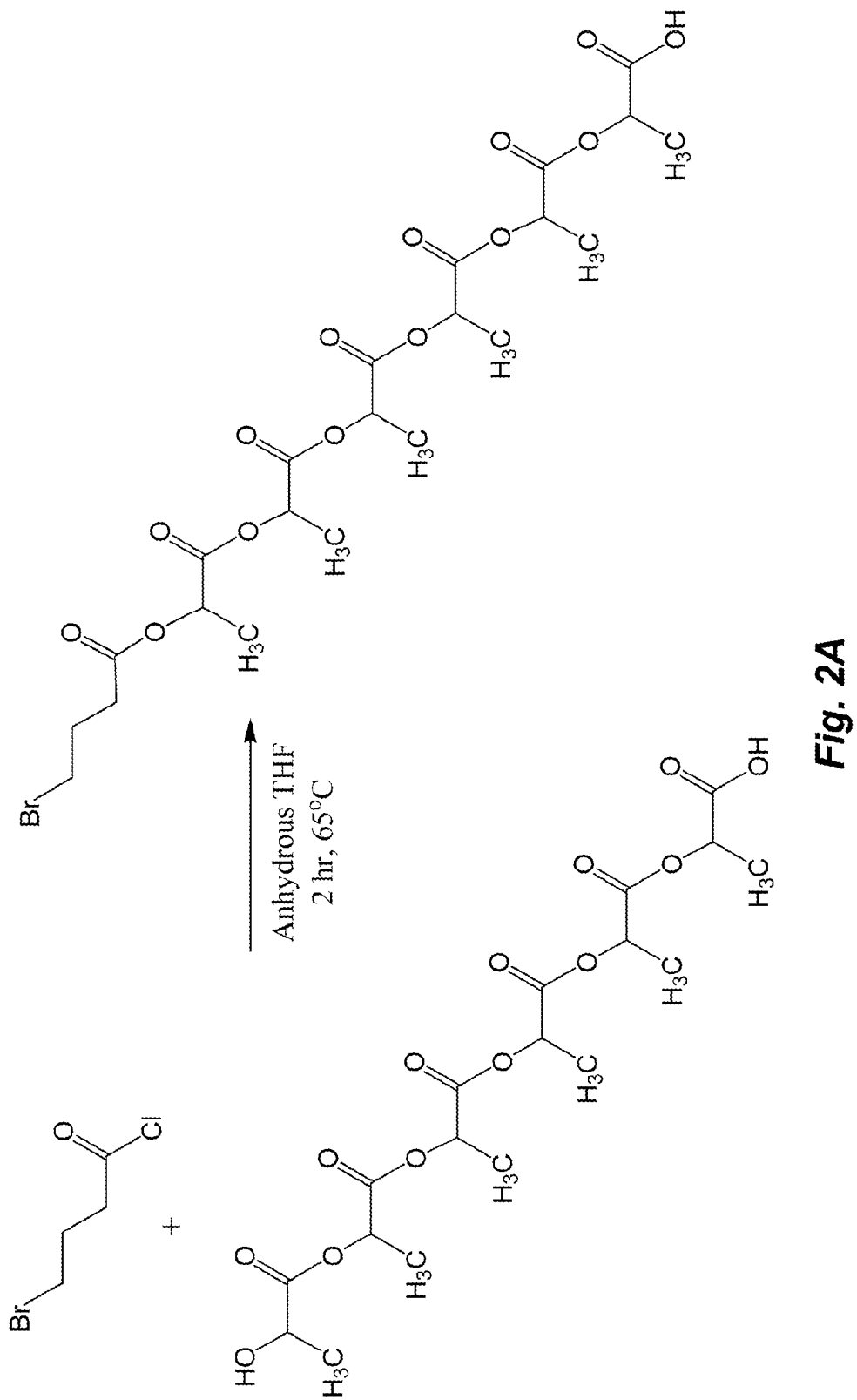
FIG. 2A and FIG. 2B show a reaction scheme of preparing a conductive plastic by functionalizing multi-walled carbon nanotubes (MWCNTs) with a thermoplastic polymer (polylactic acid).
Figure 2B:
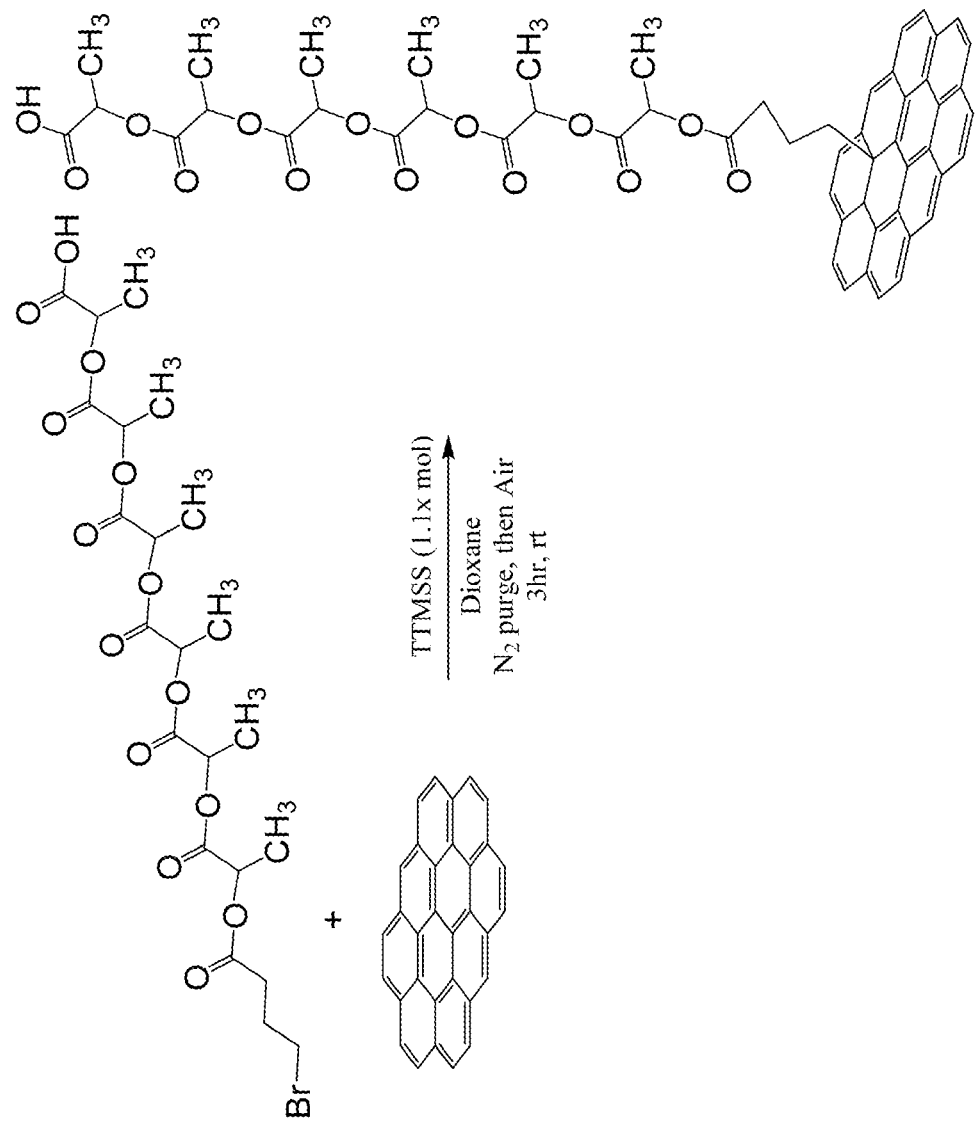

FIG. 2A and FIG. 2B illustrate an example of forming nanoparticles functionalized with a thermoplastic polymer.

FIG. 2A shows an initial step to prepare a polymer-derived functionalizing unit. In particular, a thermoplastic polymer, e.g., PLA (shown as a segment, not reprehensive of the entire polymer) is initially functionalized to provide a leaving group. As shown, PLA is first brominated at the terminal carboxylic acid by reacting with 4-bromobutyryl chloride. Other halogen-substituted acyl chlorides or halogen-substituted acid anhydride may also be used. The resulting product may be neutralized (e.g., by washing with a solvent or base such as trimethylamine) before proceeding to the next step as the functionalizing unit.

FIG. 2B shows that the brominated PLA is further coupled to one or more multi-walled CNTs (partial view of the tube is shown) in a TTMSS-mediated reaction. As a result of the functionalization, which covalently binds conductive CNTs to the PLA, the CNTs become well dispersed and the resulting product is electrically conductive.

In various embodiments, the loading of the CNTs may be from 0.5% to about 20% by weight of the PLA, in other embodiments, the CNTs may be from 1-7%, or 5-15% or 10-20% by weight of the PLA. The resulting conductive polymer has conductivity as high as 0.5 Ω/cm. Depending on the end use, the conductive PLA may be further processed through extrusion, printing (including 3D printing) and the like.

Advantageously, the CNTs are well-dispersed within the PLA matrix. Without wishing to be bound by theories, it is believed that the covalent bonds of between the CNTs and PLA overcome the van der waals interactions between the CNTs, thus causing disaggregation of CNTs. Thus, the above process of forming functionalized nanoparticles is also a process of dispersing nanoparticles.

In addition, another embodiment provides a functionalized nanomaterial comprising:
  a thermoplastic polymer; and
  a plurality of nanoparticles dispersed in the thermoplastic polymer and at least some of the nanoparticles are covalently coupled the thermoplastic polymer.

As discussed herein, the TTMSS-mediated reaction is particularly suitable for forming a composite material by employing functionalizing units having multiple leaving groups and nanoparticle substrates. Following simultaneous or sequential functionalization steps in which leaving groups are removed, radicals of the organic moiety are generated and become available to form covalent bonds with one or more types of nanoparticles. As a result, nanoparticles are connected to each other by covalent bonds via the organic moiety (Fn) of the functionalizing units. Through controllable parameters such as the molar amounts of the nanoparticle substrates, functionalizing units having multiple leaving groups of differing reactivities to TTMSS, composite materials composed of strongly bonded nanoparticles are be formed in a controllable manner.

Thus, another embodiment provides a process for forming a composite material, comprising:
  providing a first substrate;
  providing a first reaction mixture by combining with the first substrate:
    (a) a functionalizing unit represented by Fn-(X)$_m$, wherein Fn is an organic moiety, X is, at each occurrence, the same or different and independently halogen, acyl halide, isocyanide, thionoester, xanthate, selenide, isocyanate, thiocyanate, sulfide, triflate, selenocyanide, or a Barton ester covalently connected to a respective carbon atom of Fn, and m is an integer ≥2;
    (b) tris(trimethylsilyl)silane; and
    (c) a radical initiator; and
  allowing the first reaction mixture to react for a sufficient period of time to provide a functionalized first substrate comprising one or more Fn covalently attached to the surface of the first substrate, wherein the covalently attached Fn comprises at least one X group;
  combining the functionalized first substrate with a second substrate with tris(trimethylsilyl)silane and a radical initiator to form a second reaction mixture; and
  allowing the second reaction mixture to react for a sufficient period of time to provide a functionalized second substrate covalently bonded to the first substrate via Fn.

In various embodiments, the functionalizing units are bi-substituted (m=2), tri-substituted (m=3) or multi-substituted with leaving groups.

In further embodiments, if after the second substrate is functionalized and there is still X group remaining on Fn (e.g., the functionalizing unit has at least three X groups), the process may further comprises:
  combining the functionalized second substrate with a third substrate with tris(trimethylsilyl)silane and a radical initiator to form a third reaction mixture; and
  allowing the third reaction mixture to react for a sufficient period of time to provide a functionalized third substrate covalently bonded to the first substrate and the second substrate via Fn.

In various embodiments, the first, second and third substrates are first, second and third plurality of nanoparticles, as defined herein. Although the composite material typically comprises at least two different types of nanoparticles, it is also possible that the first, second and third substrates are the same type of nanoparticles. However, because of the strong covalent bonds formed during the functionalization process, depending on the type and length of the organic moiety of the functionalizing unit (Fn), the nanoparticles may be brought together and spatially arranged in a structure that is not found in nature.

In various embodiments, the first, second, third plurality of nanoparticles are the same or different and independently carbon nanotubes, particles of graphene, buckyballs, carbyne, nano-diamonds, titanium dioxide, silica, magnetite, metal nanoparticles or microparticles, semiconductor nanoparticles or microparticles, and metal oxide nanoparticles.

The TTMSS-mediated reaction allows for forming versatile composite materials by combining any two or more types of the nanoparticles by covalently bonds based on a variety of organic moiety (Fn). The organic moiety may be aryl, alkyl, alkenyl, alkynyl, cycloalkyl, cycloalkenyl, heterocyclyl or heteroaryl, or a combination thereof. Some of the Fn groups have desirable properties other than being a linkage among the nanoparticles. For instance, an electron donating tertiary-amine moiety may activate a nearby nucleophilic functional group.

As an alternative to the sequential functionalization process described above, it is also possible to simultaneously functionalize two or more types of substrates, (e.g., two types of plurality of nanoparticles) by forming a premix of all of the substrates. The premix of the substrates may be combined with TTMSS, a functionalizing unit and a radical initiator.

Alternatively, the premix substrates may be combined with a premix TTMSS reaction precursor before adding a radical initiator to initiate the functionalization steps. The functionalization steps involve covalently bonding the nanoparticles together that is akin to a curing or polymerization step, by which the nanoparticles will amalgamate into a composite material. Before the curing is complete, however, it is possible to extrude the reaction mixture or otherwise mold the reaction mixture into desired shapes.

Thus, a further embodiment provides a process of forming a composite material comprising:
  providing a premix mixture of a first substrate and a second substrate;
  providing a reaction mixture by combining the first and second substrate with:
    (a) a functionalizing unit represented by Fn-$(X)_m$, wherein Fn is an organic moiety, X is, at each occurrence, the same or different and independently halogen, acyl halide, isocyanide, thionoester, xanthate, selenide, isocyanate, thiocyanate, sulfide, triflate, selenocyanide, or a Barton ester covalently connected to a respective carbon atom of Fn, and m is an integer $\geq 2$; and
    (b) tris(trimethylsilyl)silane; and
  exposing the reaction to a radical initiator for a sufficient period of time to form covalent bonds between the first substrate and second substrate via Fn.

In more specific embodiments, the TTMSS-mediated reaction allows for forming versatile composite materials by combining any two or more types of the nanoparticles by covalently bonding via a variety of organic moiety (Fn). This type of nanocomposite is also referred to as "nanohybrid." Thus, a further embodiment provides a nanocomposite material comprising:
  a first plurality of nanoparticles;
  a second plurality of nanoparticles;
  wherein the first plurality of nanoparticles are covalently bonded to the second plurality of nanoparticles via an organic moiety, wherein the organic moiety is alkyl, alkenyl, alkynyl, cycloalkyl, cycloalkenyl, heterocyclyl or heteroaryl, or a combination thereof.

Figure 3:
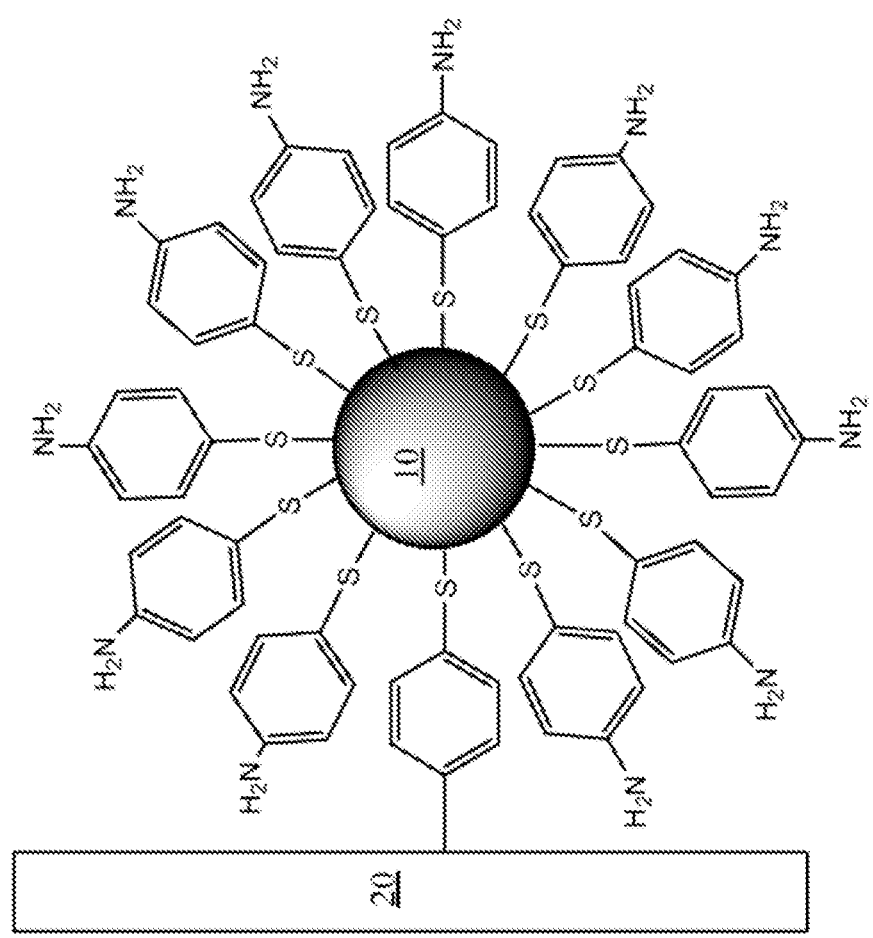
FIG. 3 shows the structure of the nanocomposite material comprising ultra-stable nanoparticles anchored on carbon nanomaterials with said nanoparticles further chemically functionalized by bi-functional or multi-functional capping molecules, in accordance with an embodiment of the invention.

In a specific embodiment, the first plurality of nanoparticles includes ultra-stable nanoparticles and the second plurality of nanoparticls includes carbon nanomaterials (CNMs). Thus, this embodiment provides a nanocomposite material comprising ultra-stable nanoparticles anchored on carbon nanomaterials (CNMs) with said nanoparticles further chemically functionalized by bi-functional or multi-functional capping molecules that include (i) metal nanoparticle stabilizing functional groups (e.g., thiol, amino, and/or carboxyl groups) on one end and (ii) a variety of functional groups on the opposite end—including but not limited to solvent and polymer compatiblizing functional groups—to (i) stabilize metal nanoparticles anchored on CNMs and (ii) increase interfacial interaction between metal nanoparticle-CNM nanohybrids and solvents or polymer matrices and/or to further anchor additional particles or chemical payloads, among other functions. FIG. 3 shows schematically a nanoparticle (10) functionalized with a bi-functional molecule (4-aminothiophenol) and anchored on a substrate (20). The bi-functional molecules are coupled to the nanoparticles by the thiol moiety, and may be further functionalized from the remaining amino moiety. As used herein, "ultra-stable nanoparticles" refer to chemically etched metal nanoparticles that are analogous to the chemically synthesized 44 atom silver nanoparticles described in Desireddy, A., et al. Nature, 501(7467), 399-402 (2013); and Yang, H., et al. Nature Communications, 4 (May) 2422 (2013). The substrate may be CNTs.

In yet another more specific embodiment, the first substrate is a macro-scale material and the second substrate is a plurality of nanoparticles. In particular, the macro-scale material is the whole or a part of an object (e.g., a device) that has a receiving surface for functionalization. The reaction can take place on the surface of the macrio-scale material as the macro-scale material is combined with the reaction premix (by dipping or coating).

In certain embodiments, the functionalizing unit and TTMSS may be a premix reaction precursor. In other embodiments, they may be separately combined with the premix mixture of the first substrate and the second substrate.

In further embodiments, the premix mixture further comprises a third substrate, which may be a plurality of nanoparticles.

FIG. 4A-FIG. 4D show the reaction schemes of forming a composite having two types of nanoparticles: ultra-stable silver nanoparticles anchored on CNTs.

Figure 4A:
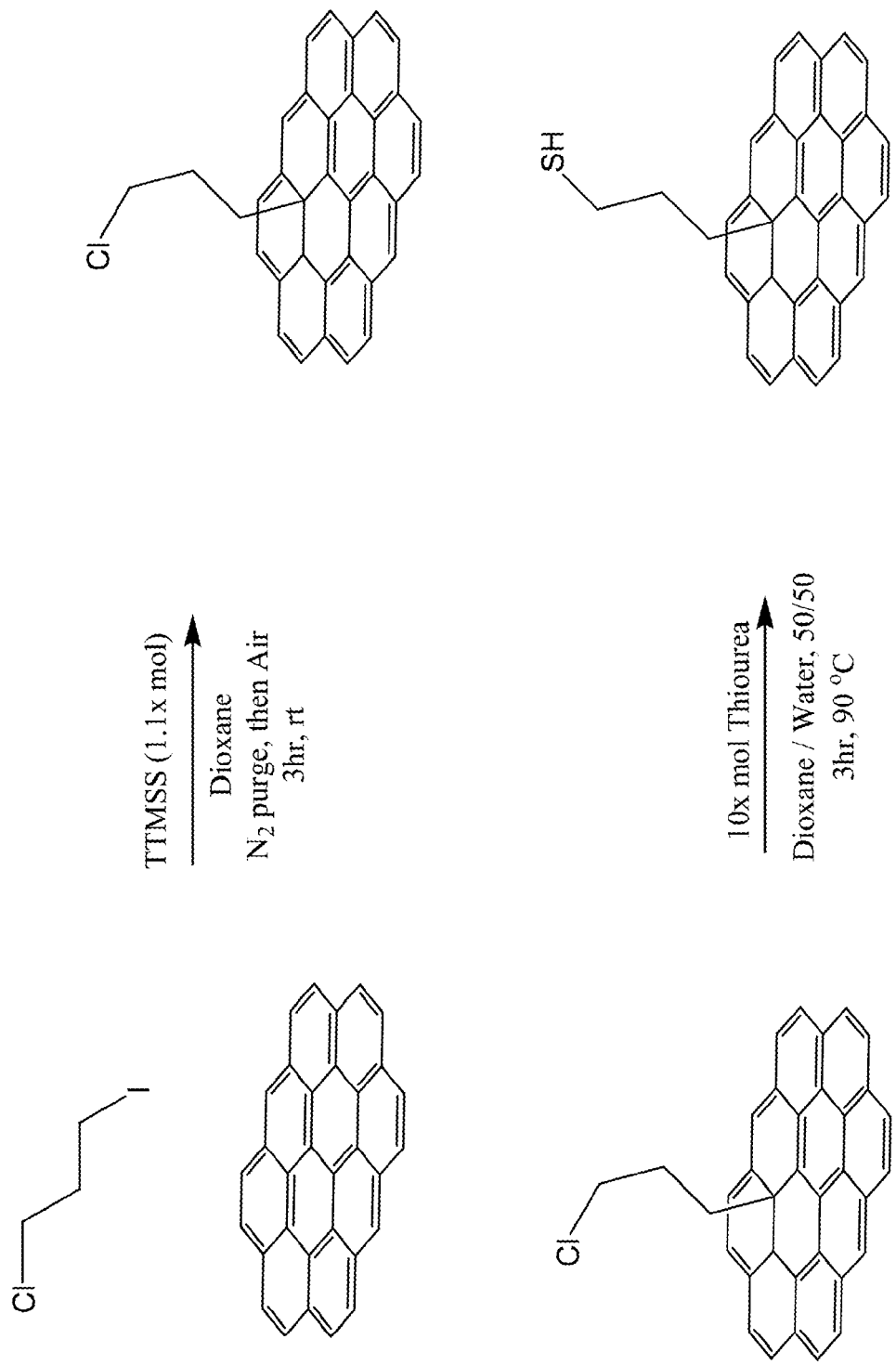
FIG. 4A-FIG. 4D show a reaction scheme of preparing a conductive plastic functionalized with silver nanoparticles, which are in turn functionalized with MWCNTs.

FIG. 4A shows that CNTs are functionalized by a thiolpropyl group via a TTMSS-facilitated coupling reaction as described herein.

Figure 4B:
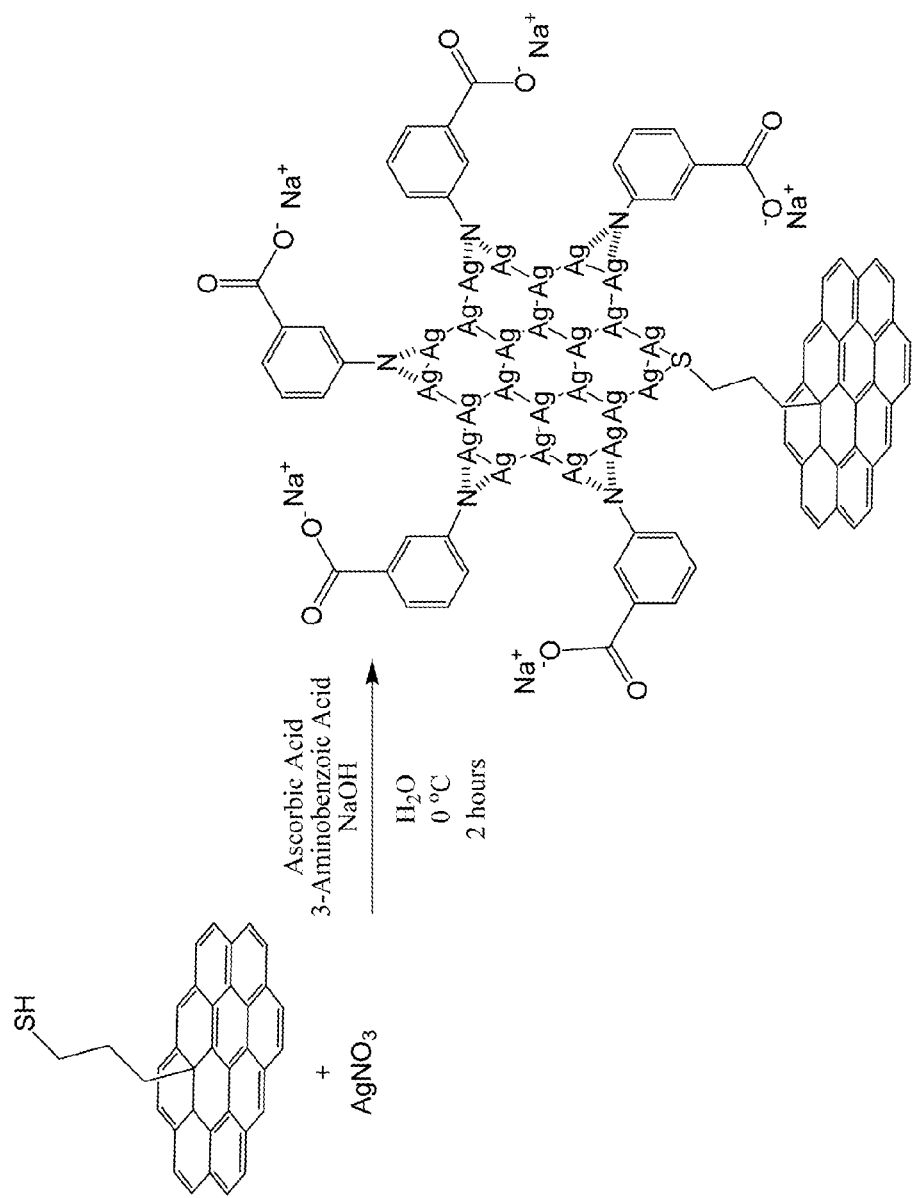

FIG. 4B shows that the thiol-functionalized CNTs acts as an anchor to nucleate silver atoms out of a silver salt solution (e.g., silver nitrate) via a reduction reaction (e.g., using ascorbic acid as a reducing agent). The in-situ produced ultra-stable silver nanoparticles as has 44 silver atoms and is further bound to 30 3-aminobenzoic acid (3-ABA) molecules (not all silver atoms or 3-ABA molecules are shown). The resulting compound is a silver nanoparticle capped with 3-ABA and functionalized with CNTs.

Figure 4C:
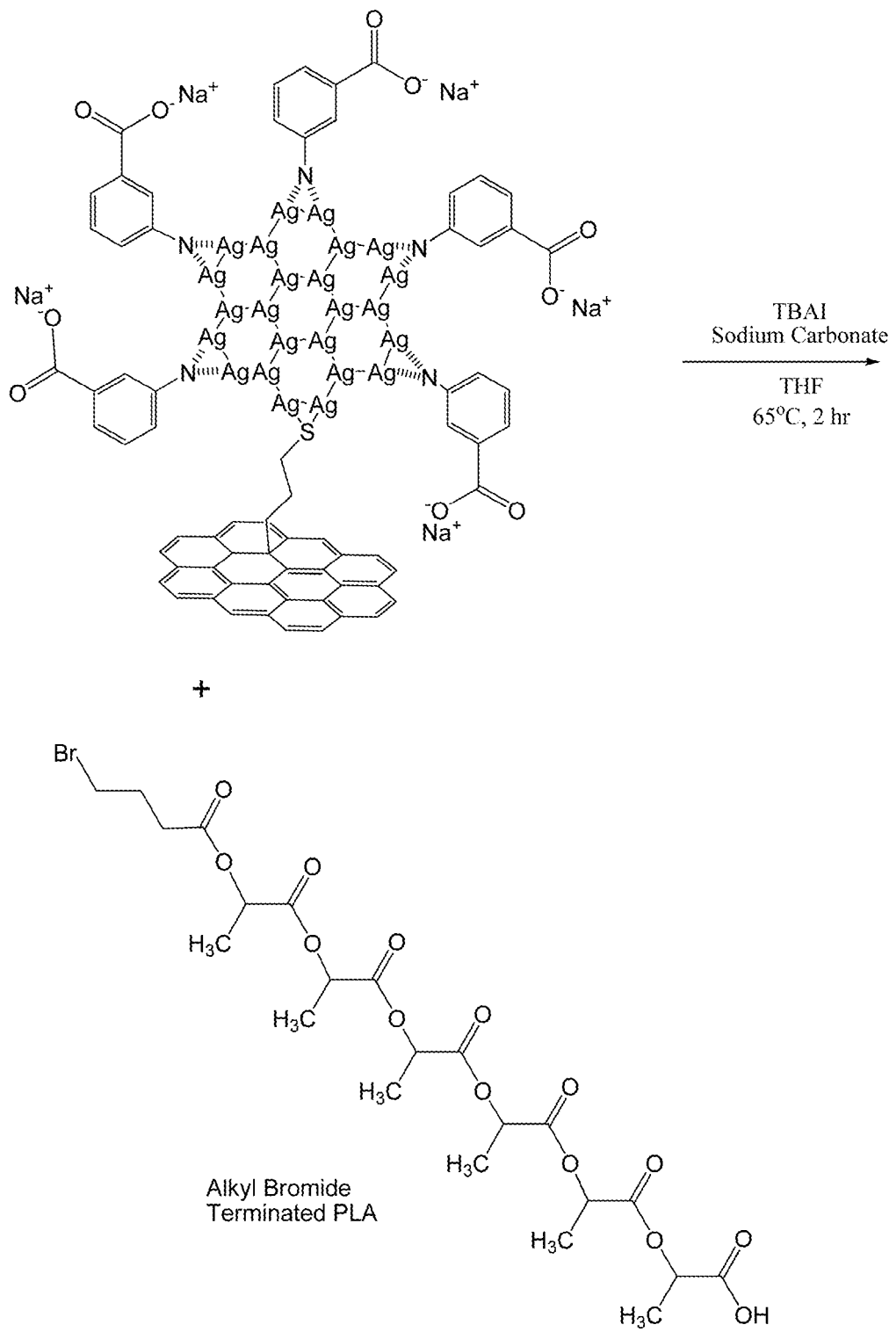
Figure 4D:
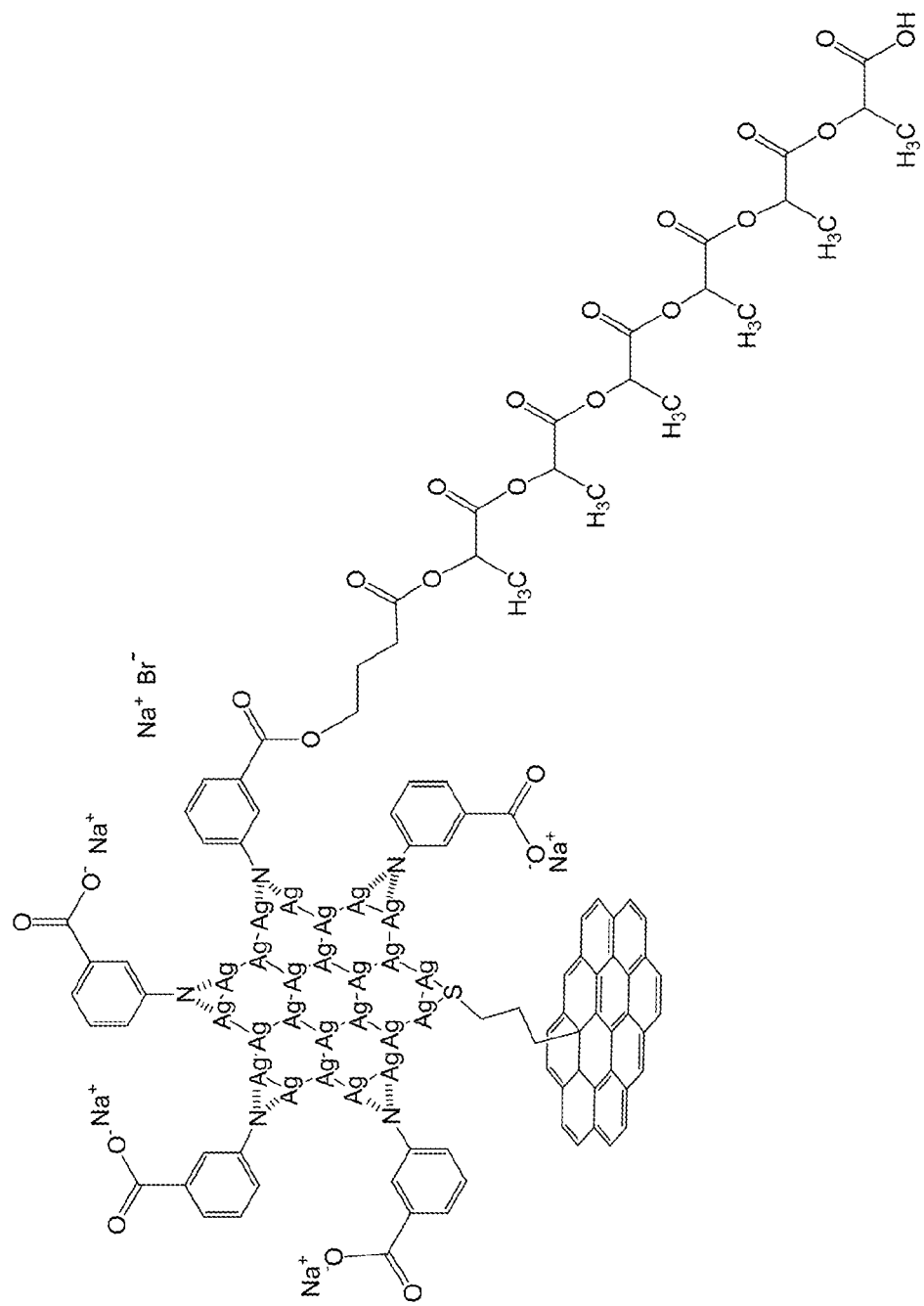

FIG. 4C and FIG. 4D show that the capped silver nanoparticle is further coupled to a bromobutyrrylated polylacitic acid (PLA) to produce a conductive plastic.

According to one aspect of the invention, an application of the general methods of the present invention is provided. The application functionalizes CNTs in such a way as they may be separated by metallic character and subsequently bonded to gold nanoparticles to form gold nanoparticle-metallic CNT nanohybrids. In such a process, minimally reacted semi-conducting CNTs are separated as a secondary product.

According to one aspect of the invention, an application of the general methods of the present invention is provided. The application functionalizes carbon nanomaterials in such a way as they may be converted to thiol functionalized carbon nanomaterials and subsequently, metal nanoparticle-carbon nanomaterial nanohybrids.

According to one aspect of the invention, an application of the general methods of the present invention is provided. The application functionalizes metal nanoparticles in such a way as they may be chemically and thermally stabilized and concurrently primed for grafting to a nanomaterial or macromaterial.

According to one aspect of the invention, an application of the general methods of the present invention is provided. The application functionalizes metal nanoparticles in such a way as they may be chemically and thermally stabilized and concurrently primed for grafting from a functionalized nanomaterial or macromaterial.

According to one aspect of the invention, an application of the general methods of the present invention is provided. The application functionalizes nanomaterials, including nano-diamonds, carbon nanotubes, and boron nitride nanotubes, in such a way as to cross-link the nanomaterials to from a hard and strong nanocomposite material. In some embodiments of the present process, a ternary epoxy-like compound is formed for this purpose, comprising an "uncured" nanomaterial powder, a TTMSS solution, and a "functionalizing unit" solution. In some embodiments of the process to crosslink nanomaterials, a binary epoxy-like compound is formed, comprising an "uncured" nanomaterial mixture and a TTMSS solution.

The method herein disclosed can include the steps of: providing a substrate consisting of a nano- or macro-material; immersing said substrate in a solvent; adding to the same mixture one or more "functionalizing units", which contain bonds between carbon and halogen, acyl halide, isocyanide, thionoester, xanthate, selenide, isocyanate, thiocyanate, sulfide, triflate, selenocyanide, or a Barton ester, respectively; adding to the same mixture Tris(Trimethylsilyl) Silane (TTMSS): exposing said mixture to air under stirring; quenching the reaction; repeating addition of TTMSS and stirring of mixture under air as needed with or without further addition of substrates or "functionalizing units". In some embodiments, the quenching can be carried out by flowing ambient air.

In the preferred embodiments of the present invention, deionized water is used as the solvent in conjunction with a water-insoluble "functionalizing unit" and water-insoluble TTMSS. In some embodiments, a mixture of water and dixoane, or a mixture of water and another non-polar and water-miscible solvent is used as the solvent. Use of such a mixed solvent is appropriate when solvated substrates or "functionalizing units" that do not solvate in water alone are desired. Solvents, however, should exclude methanol and other alcohols as such chemicals rapidly decompose TTMSS. In other embodiments, low-boiling point solvents may be used, such as MTBE to expedite drying.

In the preferred embodiments of the present invention, "functionalizing units" comprise molecules, compounds, nano-materials, or macro-materials that contain one or more bonds formed between carbon and one of the following groups: halogen, acyl halide, isocyanide, thionoester, xanthate, selenide, isocyanate, thiocyanate, sulfide, triflate, selenocyanide, or a Barton ester. Preferably, the carbon-halogen bonds of said "functionalizing units" are between carbon and Cl, Br, or I. Preferably, additional bonds of said "functionalizing units" are between carbon isocyanides, thionoester, xanthate, selenides (e.g., phenyl selenide), isocyanate, thiocyanate, sulfides (e.g., phenyl sulfide), triflates, and selenocyanides. "Functionalizing units" may also include other functional groups and functional group precursors, but preferably those which will not react at a higher rate with TTMSS than leaving groups (as defined herein) to be cleaved and further that will not react appreciably with the subsequently generated radical itself. In some embodiments of the present invention, the "functionalizing unit" is an organic halide, including alkyl, acyl, or aryl halides. Use of such "functionalizing units" according to the methods discussed herein form reactive alkyl, acyl, or aryl radicals respectively, radicals that react with substrates to form covalent carbon-substrate bonds. In other embodiments of the present invention, the "functionalizing unit" is a non-cyclic organic molecule with a conjugated portion and at least one carbon-Barton ester bond at a terminal carbon of the conjugated portion. Use of such "functionalizing units" according to the methods discussed herein form reactive radicals at the terminal carbon of the conjugated portion of the "functionalizing units" via a Barton decarboxylation reaction. Radicals so formed react with substrates to form covalent carbon-substrate bonds that are further conjugated through the conjugated portion of the "functionalizing unit". In other embodiments, the "functionalizing unit" is a compound comprising a metal nanoparticle capped by a molecule containing halogen, acyl halide, isocyanide, thionoester, xanthate, selenide, isocyanate, thiocyanate, sulfide, triflate, selenocyanide, or a Barton ester. In some embodiments of the present invention, "functionalizing units" contain a combination of different leaving groups, including halogen, acyl halide, isocyanide, thionoester, xanthate, selenide, isocyanate, thiocyanate, sulfide, triflate, selenocyanide, or a Barton ester so that as the method is repeated with more TTMSS and stirring, the most reactive leaving group of said "functionalizing unit" form carbon-substrate bonds first, followed sequentially by the less reactive leaving group of the same "functionalizing unit" upon subsequent additions of TTMSS and stirring under air. For example, some embodiments of the present invention employ multi-functional "functional units" with carbon-iodine, carbon-bromine, and carbon-chlorine bonds so that carbon-iodine bonds form carbon-substrate bonds first, followed sequentially by carbon-bromine and then carbon-chlorine bonds upon subsequent additions of TTMSS and stirring under air.

"Functionalizing units" that contain one or more leaving groups such as halogen, isocyanides, thionoester, xanthate, selenides (e.g., phenyl selenide), isocyanate, thiocyanate, sulfides (e.g., phenyl sulfide), triflates, and selenocyanides may be purchased commercially or be prepared according to known methods in the art. For example, suitable compounds such as iodobenzene, bromobenzene, 1,4-diiodobenzene, 3-chloro-1-iodopropane, 1,4-dibromobenzene, 1-bromo-4-iodobenzene, and phenyl isocyanate are commercially available. A person of ordinary skill in the prior art may also prepare "functionalizing units" that contain one or more carbon-Barton ester bonds. In the preferred embodiments of the present invention, TTMSS is used as a non-toxic and environmentally friendly radical reducing agent. In other embodiments of the present invention, tributyltin hydride may be used in lieu of TTMSS as the radical reducing agent.

In the preferred embodiments of the present invention, the reaction mixture containing the substrate, the "functionalizing units", and TTMSS are stirred under ambient air at room temperature. Preferably, solvent, substrate, and "functionalizing unit" are degassed together prior to introduction of TTMSS to purge the mixture of dissolved oxygen and carbon dioxide. Doing so ensures controlled formation of TTMSS radicals via reaction of TTMSS with dioxygen in the ambient air. Preferably the mixture is stirred under ambient air or exposed via forced air bubbling for at least 2 hours in order to ensure adequate reaction. Optimal stirring times, however, vary with different substrates and "functionalizing units". In some embodiments of the present invention, radical initiators including but not limited to benzoyl peroxide, lauryl peroxide, AIBN, and ACCN may be used in lieu of air, under an inert atmosphere.

In the preferred embodiments of the present invention, the reaction mixture containing the substrate, the "functionalizing units", and TTMSS, is stirred under flowing ambient air following adequate reaction time to quench reaction radicals and prevent further reaction.

Advantageously, the present invention is capable of utilizing multiple functional groups as points for either single substrate attachment or to carry multiple reactive functional groups to be used in sequential synthesis by using molar amounts of TTMSS to activate only the most reactive functional groups on the target molecules, resulting an easy to control, sequential functionalization process. Such an advantage allows the use of a bi, tri, or otherwise polyfunctional molecule to be used as a multistep precursor for functionalization.

Advantageously, the preferred embodiments of the methods disclosed herein avoid the use of explosive diazonium salts and diazonium intermediates.

Advantageously, the methods disclosed herein represent an inexpensive, fast, and scalable process for nanocomposite material manufacture.

Advantageously, in some embodiments of the present invention, the methods disclosed provide a one-pot method to manufacture nanocomposite materials.

In some embodiments of the present invention, the method disclosed herein is used to functionalize CNTs in such a way as they may be separated by metallic character and subsequently bonded to gold nanoparticles to form gold nanoparticle-metallic CNT nanohybrids. In such a process, minimally reacted semi-conducting CNTs are separated as a secondary product. Such a process may employ a CNT substrate, a dioxane solvent, TTMSS, and a tri-functional "functionalizing unit" with carbon-halogen bonds of varying reactivity toward TTMSS radicals, such as 1-bromo-3-chloro-5-iodobenzene. Such a process begins with stirring of CNTs, 1-bromo-3-chloro-5-iodobenzene, and TTMSS in a flask containing dioxane, which preferably, though not necessarily, has been purged from dissolved oxygen and carbon dioxide. Stirring of the mixture continues under ambient air for 2 hours at room temperature. In such a process, dioxygen from ambient air firstly abstracts hydrogen from TTMSS to from a TTMSS radical and a hydroperoxyl radical. Secondly, the TTMSS radical abstracts iodine from 1-bromo-3-chloro-5-iodobenzene to form an aryl radical. At this step, the TTMSS radical largely leaves bromine and chlorine of 1-bromo-3-chloro-5-iodobenzene undisturbed due to more favorable energetics in the radical's reaction with iodine. Thirdly, the aryl radical reacts with a CNT to form a carbon-carbon bond between 1-bromo-3-chlorobenzene and the CNT. At this step, the aryl radical largely leaves semi-conducting CNTs undisturbed due to greater reactivity of aryl radicals toward metallic CNTs. Aryl radicals so formed through the methods of the present invention, therefore, exhibit reactive selectivity for metallic CNTs analogous to selectivity observed in aryl diazonium reagents of the prior art toward the same metallic CNTs.

In some embodiments of the present invention, the 1-bromo-3-chlorophenyl functionalized metallic CNTs are further converted to magnetite functionalized metallic CNTs with magnetic properties. In such a process, the 1-bromo-3-chlorophenyl functionalized metallic CNTs as prepared above are preferably degassed again and after adding additional TTMSS, stirred under ambient air in the same reaction vessel to form new TTMSS radicals that now abstract bromines from said 1-bromo-3-chlorophenyl functionalized metallic CNTs to yield CNT anchored aryl radicals. Such aryl radicals react in the presence of excess magnetite nanoparticles to form carbon-metal bonds, yielding magnetite nanoparticle-metallic CNT nanohybrids. Additional stirring time must be afforded at this step to ensure adequate reaction between the TTMSS radical and the less reactive bromine from 1-bromo-3-chlorophenyl functionalized metallic CNTs (as compared to the iodine from 1-bromo-3-chloro-5-iodobenzene).

In some embodiments of the present invention, such magnetite nanoparticle-metallic CNT nanohybrids may be collected by magnets through the glass wall of a glass reactor with stirring to separate magnetite functionalized metallic CNTs from unreacted semi-conducting CNTs. Unreacted—and as a result, nonmagnetic—semi-conducting CNTs may also be separated at this step. Optionally, sulfuric acid may be added after separation to dissolve magenitite particles if magnetic CNTs are not desired for subsequent steps. Optionally, separated magnetite functionalized metallic CNTs may be immersed in concentrated sulfuric acid to both dissolve magnetite particles as well as effectively disperse the CNTs without damaging them for subsequent steps.

In some embodiments of the present invention, the functionalized metallic CNTs described above—whether treated with sulfuric acid or not—are first degassed, and again stirred under ambient air in the presence of additional TTMSS, and added gold nanoparticles to yield gold nanoparticle-metallic CNT nanohybrids. Excess TTMSS and additional stirring time must be afforded at this step to ensure adequate reaction between the TTMSS radical and the less reactive chlorine from 3-chlorophenyl functionalized metallic CNTs.

In some embodiments of the present invention, the method disclosed herein is used to functionalize carbon nanomaterials in such a way as they may be converted to thiol functionalized carbon nanomaterials and subsequently, metal nanoparticle-carbon nanomaterial nanohybrids. As used herein, a carbon nanomaterial (CNM) refers to forms of graphitic carbon having conjugated, repeating, aromatic carbon rings including but not limited to Carbon Nanotubes (CNTs), graphene, Buckyballs, nanoribbons, carbyne, and nano-diamonds. Such a process may employ a CNT substrate, a dioxane solvent, TTMSS, and a bi-functional "functionalizing unit" with carbon-halogen bonds of varying reactivity toward TTMSS radicals, such as 1-bromo-4-iodobenzene. Such a process begins with stirring of CNTs, 1-bromo-4-iodobenzene, TTMSS in a flask containing dioxane, which preferably, though not necessarily, has been purged from dissolved oxygen and carbon dioxide. Stirring of the mixture continues under ambient air for 2 hours at room temperature to yield a 4-bromophenyl functionalized carbon nanomaterial.

In some embodiments of the present invention, thiourea is reacted with such a 4-bromophenyl functionalized carbon nanomaterial in a solvent less polar than water at greater than 80° Celsius to substitute CNM attached alkyl as well as aryl halides with thiol chemical functional groups to provide a thiol functionalized CNM.

In some embodiments of the present invention, high-solubility metal salts and reducing agents are mixed with such a thiol functionalized CNM to synthesize and deposit metal nanoparticles on thiol chemical anchors of the thiol functionalized CNMs. In such a reaction, high-solubility metal salts are added to thiol functionalized CNMs to form metal ions attracted to the thiol chemical anchors. Appropriate metals salts include but are not limited to the methanesulfonate and/or nitrate salts of cobalt, nickel, copper, lead, palladium, silver, gold, or platinum. Reducing agent is subsequently added drop wise to reduce metal ions to form metal nanoparticles on CNMs. These steps yield metal nanoparticle-CNM nanohybrids.

In some embodiments of the present invention, such metal nanoparticle-CNM nanohybrids are further functionalized with bi-functional or multi-functional capping molecules that include (i) metal nanoparticle stabilizing functional groups (e.g., thiol, amino, and/or carboxyl groups) on one end and (ii) a variety of functional groups on the opposite end—including but not limited to solvent and polymer compatiblizing functional groups—to (i) stabilize metal nanoparticles anchored on CNMs and (ii) increase interfacial interaction between metal nanoparticle-CNM nanohybrids and solvents or polymer matrices and/or to further anchor additional particles or chemical payloads, among other functions.

In some embodiments of the present invention, bi-functional or multi-functional capping molecules that include a thiol functional group on one end are mixed with a silver metal nanoparticle-CNM nanohybrid prepared according to the methods described above to convert such a silver nanoparticle-CNM nanohybrid to an ultra-stable silver nanoparticle-CNM nanohybrid. As used herein, an "ultra-stable nanoparticle" refers to a chemically etched metal nanoparticle that is analogous to the chemically synthesized 44 atom silver nanoparticles described in (Desireddy et al., 2013; Yang et al., 2013). In such a process, adding thiol functionalized capping agents to silver nanoparticle-CNM nanohybrids etch and cap CNM-anchored silver nanoparticles into ultra-stable 44 atom silver nanoparticles without detaching said silver nanoparticles from their CNMs. Such a process stabilizes CNM anchored nanoparticles sufficiently to yield metal functionalized CNM nanohybrids processable, for example, in scalable industrial processes ideal for polymer nanocomposite manufacture.

In some embodiments of the present invention, a variety of functional groups may be employed on the ends of the capping molecule opposite the metal nanoparticle stabilizing groups to impart desired characteristics (e.g., water-solubility, surface properties, electrical properties, biocompatibility) to the metal nanoparticle-CNM nanohybrid functionalized with said capping molecule.

In some embodiments of the present invention, the capping molecule may be functionalized to alter the compatibility of the metal nanoparticle-CNM nanohybrid with respect to a solvent. For example, the capping molecule may be functionalized with one or more hydrophilic groups to enhance the solubility of the nanohybrid with aqueous solvents, such as water. Examples of such hydrophilic groups include, but are not limited to, amines, hydroxyls, carboxylic acids, carboxylates, sulfates, and phosphates. As a an example, adding 4-mercaptobenzoic acid capping molecules to thiol functionalized, silver nanoparticle-CNM nanohybrids with an average of 3-6 nm silver nanoparticles will (i) etch and cap CNM-anchored silver nanoparticles into ultra-stable 44 atom silver nanoparticles without detaching them from their CNMs and (ii) introduce up to 29 additional carboxyl functional groups, strongly bonded to the silver nanoparticles, to increase interfacial interaction between the silver nanoparticle-CNM nanohybrids and water.

In some embodiments, the capping molecule may be functionalized to alter the compatibility of the metal nanoparticle-CNM nanohybrid with respect to a polymeric material. For example, the capping molecule may be functionalized with functional groups that allow the nanohybrid to be soluble or miscible with a polymer matrix. The functional groups may be selected to impart compatibility with a particular material. This may enable the formation of polymer blends comprising metal nanoparticle-CNM nanohybrids. As an example, adding 4-aminothiophenol dissolved in a water miscible alcohol to thiol functionalized silver nanoparticle-CNM nanohybrids in a strongly basic solution will (i) etch and cap CNM-anchored silver nanoparticles into ultra-stable 44 atom silver nanoparticles without detaching them from their CNMs and (ii) introduce amino functionalities to increase interfacial interaction between the silver nanoparticle-CNM nanohybrid and nylon. As another example, adding 4-cyanothiophenol capping molecules to silver nanoparticle-CNM nanohybrids will (i) etch and cap CNM-anchored silver nanoparticles into ultra-stable 44 atom silver nanoparticles without detaching them from their CNMs and (ii) introduce nitrile functional groups that increase interfacial interaction between the silver nanoparticle-CNM nanohybrid and ABS.

In some embodiments, the capping molecule may be functionalized to permit preparation of more complex, functional molecules directly from the metal nanoparticle-CNM nanohybrid. As an example, adding thiophenol capping molecules, followed by diazonium-based salts to silver nanoparticle-CNM nanohybrids will first etch and cap CNM-anchored silver nanoparticles into ultra-stable 44 atom silver nanoparticles without detaching them from their CNMs and then synthesize conductive azo dyes from the aryl ends of the thiophenol capping molecules that will enhance electrical conductivity of the nanomaterial as well as imbue the nanomaterial with stable color.

In some embodiments of the present invention, the capping molecule may be functionalized to permit polymerization of functional polymers directly from the metal nanoparticle-CNM nanohybrid. For example, adding mercaptoaniline as the capping molecule, followed by the addition of aniline or methoxyaniline along with an oxidizing agent, such as ammonium peroxidisulfate and a protonic dopant, such as dodecylbenzylsulfonic acid, each in a 1:1:1 molar ratio, will copolymerize intrinsically conductive, solvent processable polyaniline directly with the functional capping molecules of the CNM nanohybrid material.

In some embodiments of the present invention, the method disclosed herein is used to functionalize metal nanoparticles in such a way as they may be chemically and thermally stabilized and concurrently primed for grafting to a nanomaterial or macromaterial. In some embodiments of the present process to functionalize metal nanoparticles, a metal nanoparticle substrate, a "functionalizing unit", and TTMSS are stirred under ambient air. Preferably, for such a process under ambient air, the stoichiometric ratios of the substrate, the "functionalizing unit" and TTMSS used are adjusted to limit unwanted side reactions: such as oxidation of metal nanoparticles and attachment of TTMSS radicals to oxidized metal nanoparticles. For example, such a process may employ TTMSS in a stoichiometric amount greater than or equal to the stoichiometric amount of metal atoms on the surface of the metal nanoparticle substrate provided in order to favor formation of TTMSS radicals and minimize oxidation of metal nanoparticles, Further, such a process may employ "functionalizing units" in a stoichiometric amount greater than or equal to twice the stoichiometric amount of TTMSS provided in order to favor TTMSS radical reaction with "functionalizing units" and minimize TTMSS radical attachment to oxidized metal nanoparticles. Preferably, such a process under ambient air and stoichiometric management also employs bi-functional and sterically hindered "functionalizing units" in order to limit unwanted polymerization of the "functionalizing units" provided. As used herein, a bi-functional and sterically hindered "functionalizing unit" refers to an aryl halide with at least two leaving groups selected from halogen, acyl halide, isocyanide, thionoester, xanthate, selenide, isocyanate, thiocyanate, sulfide, triflate, selenocyanide, and a Barton ester, and at least one of an alkyl substituent or "unreactive" (minimally reactive toward TTMSS radicals) heteroatom substituent (e.g., —F, —Cl) attached to other carbons. For example, bi-functional and sterically hindered "functionalizing units" include but are not limited to 1,4-diiodo-2,5-dimethylbenzene, 1,4-dibromo-2,5-dimethylbenzene, 1-bromo-2,6-dimethyl-4-iodobenzene, 1-bromo-2,5-dimethyl-iodobenzene, 1,4-diiodo-2,3,5,6-tetramethylbenzene, 1,4-dibromo-2,3,5,6- tetramethylbenzene, 3,5-diiodo-1-chlorobenzene, 1,3-dibromo-5-chlorobenzene, 1,3-diiodo-5-fluorobenzene, 1,3-dibromo-5-fluorobenzene, 1,4-diiodotetrachlorobenzene, 1,4-dibromotetrachlorobenzene, 1,4-diiodotetrafluorobenzene, and 1,4-dibromotetrafluorobenzene. Such a process begins with stirring of metal nanoparticles, bi-functional and sterically hindered "functionalizing units", and TTMSS in a flask with solvent, which preferably has been purged from dissolved oxygen and carbon dioxide. Stirring of the mixture continues under ambient air for 2 hours at room temperature during which time bi-functional and sterically hindered "functionalizing units" form carbon-metal bonds with the metal nanoparticles provided. Such carbon-metal bonds chemically and thermally stabilize the metal nanoparticles provided. Further, such carbon-metal bonds robustly attach to the metal nanoparticles the bi-functional and sterically hindered "functionalizing units" provided, and in so doing, functionalize said metal nanoparticles with one or more functionalizing units that prime the metal nanoparticle for grafting to a nanomaterial and/or a macromaterial. Addition of TTMSS to the metal nanoparticles so functionalized, with stirring under ambient air in the presence of a nanomaterial or a macromaterial forms new carbon-carbon linkages between the metal nanoparticles so functionalized and the nanomaterial or macromaterial provided.

In some embodiments of the present invention, the method disclosed herein is used to functionalize metal nanoparticles in such a way as they may be chemically and thermally stabilized and concurrently primed for grafting from a functionalized nanomaterial or macromaterial. In such a process, methodologies and reactants match those for the method disclosed herein to functionalize metal nanoparticles in such a way as they may be chemically and thermally stabilized and concurrently primed for grafting to a nanomaterial or macromaterial except for one detail: use of mono-functional and sterically hindered "functionalizing units" instead of bi-functional and sterically hindered "functionalizing units". As used herein, a mono-functional and sterically hindered "functionalizing unit" refers to an aryl halide with a single carbon-leaving group bond, and at least one of an alkyl substituent or "unreactive" (minimally reactive toward TTMSS radicals) heteroatom substituent (e.g., —F, —Cl) attached to a carbon atom not engaged any of the above bonds. For example, mono-functional and sterically hindered "functionalizing units" include but are not limited to 1-Iodo-3,5-dimethylbenzene, 1-Iodo-2,3-dimethylbenzene, 1-bromo-3,5-dimethylbenzene, 1-bromo-2,3-dimethylbenzene, 1,3-dichloro-5-iodobenzene, 1-bromo-3,5-dichlorobenzene, 1,3-difluoro-5-iodobenzene, and 1-bromo-3,5-difluorobenzene. Similar to the process of disclosed herein, the mono-functional and sterically hindered "functionalizing units" form carbon-metal bonds with the metal nanoparticles provided. Such carbon-metal bonds chemically and thermally stabilize the metal nanoparticles provided. Further, such carbon-metal bonds robustly attach to the metal nanoparticles the mono-functional and sterically hindered "functionalizing units" provided, and in so doing, functionalize said metal nanoparticles with aryl carbons to which "functionalizing units" from functionalized nanomaterials or macromaterials may form new carbon-carbon linkages upon addition of TTMSS and additional stirring under ambient air.

In some embodiments of the present invention, appropriate metal nanoparticles for the method of functionalizing metal nanoparticles as disclosed herein include the nanoparticles of metals and metal alloys. As used herein, the term metal indicates an element that readily loses electrons to form positive ions (cations) and forms metallic bonds between other metal atoms (forming ionic bonds with non-metals); the term metal alloys indicate a solid solution or homogeneous mixture of two or more elements, at least one of which is a metal, which itself has metallic properties. Exemplary metals include but are not limited to transition metals and metalloids, and more particularly to titanium, vanadium, chromium, manganese, cobalt, nickel, copper, zinc, zirconium, molybdenum, ruthenium, rhodium, palladium, cadmium, tungsten, rhenium, osmium, iridium, platinum, gold, aluminum, bismuth, zinc, gallium, lead, and silicon. Exemplary metal alloys include but are not limited to $Pt_3Co$, and other alloys of cobalt and alloys of copper. In the embodiments of the present invention that use boron nitride nanoparticles, the "functionalizing unit" used to functionalize the boron nitride nanoparticle is a functionalized derivative of a thiophene rather than a functionalized derivative of benzene, Exercise due caution and follow proper handling procedures when using pyrophoric metal nanoparticles for the purposes of the methods disclosed herein. Pyrphoric metal nanoparticles including but not limited to the finely divided nanoparticles of cobalt, iron, aluminum, magnesium, zirconium, titanium, bismuth, zinc, and osmium may be water reactive and ignite spontaneously or react violently on contact with air, moisture in the air, oxygen, or water. Failure to follow proper handling procedures can result in fire or explosion, leading to serious injuries, death, and/or significant damage to facilities.

In some embodiments of this inert-environment process to functionalize metal nanoparticles, a radical initiator including but not limited to benzoyl peroxide, lauryl peroxide, AIBN, and ACCN may be used in lieu of air, under an inert atmosphere. In such a process, stoichiometric management of reagents to limit unwanted side reactions and use of sterically hindered "functionalizing units" is not imperative. In preferred embodiments of the present process, mono-functional or bi-functional "functionalizing units" are used to functionalize metal nanoparticles in such as a way as they may be chemically and thermally stabilized and concurrently primed for grafting to a nanomaterial or macromaterial or grafting from a functionalized nanomaterial or macromaterial, respectively. Such "functionalizing units" include but are not limited to iodobenzene, bromobenzene, 1,4-diiodobenzene, 1,4-dibromobenzene, and 1-bromo-4-iodobenzene. Such a process begins with stirring of metal nanoparticles and "functionalizing units" in solvent, which preferably has been purged from dissolved oxygen and carbon dioxide. The reaction vessel is subsequently maintained under an oxygen- and moisture-free inert environment. A radical initiator is then added to the inert-environment reaction vessel containing the metal nanoparticle. The resultant mixture is then under an inert-atmosphere for 4 hours at room temperature during which time "functionalizing units" form carbon-metal bonds with the metal nanoparticles provided. Such carbon-metal bonds chemically and thermally stabilize the metal nanoparticles provided. Further, such carbon-metal bonds robustly attach to the metal nanoparticles the "functionalizing units" provided. In the embodiment of the present inert-environment process that employs mono-functional "functionalizing units", the "functionalizing units" functionalize the metal nanoparticles provided with aryl carbons to which "functionalizing units" from functionalized nanomaterials or macromaterials may form new carbon-carbon linkages upon addition of TTMSS, and additional stirring under ambient air. In the embodiment of the present inert-environment process that employs bi-functional "functionalizing units", the "functionalizing units" functionalize the metal nanoparticles provided with one or more bonds formed between carbon and one of the following groups: halogen, acyl halide, isocyanide, thionoester, xanthate, selenide, isocyanate, thiocyanate, sulfide, triflate, selenocyanide, or a Barton ester, that prime the metal nanoparticle for grafting to a nanomaterial and/or a macromaterial. Addition of TTMSS to the metal nanoparticles so functionalized, with stirring under ambient air in the presence of a nanomaterial or a macromaterial forms new carbon-carbon linkages between the metal nanoparticles so functionalized and the nanomaterial or macromaterial provided.

In some embodiments of the inert-environment processes to functionalize metal nanoparticles, a mono-functional "functionalizing unit" with a carboxylic acid group, including but not limited to, 4-iodobenzoic acid and 4-bromobenzoic acid is stirred with a copper or aluminum nanoparticles in an organic solvent under an inert environment to form monodentate covalent bonds between a copper or aluminum nanoparticle and a "functionalizing unit". The "functionalizing units" so attached to a copper or aluminum nanoparticle functionalize the metal nanoparticles provided with one or more bonds formed between carbon and one of the following groups: halogen, acyl halide, isocyanide, thionoester, xanthate, selenide, isocyanate, thiocyanate, sulfide, triflate, selenocyanide, or a Barton ester, which prime the metal nanoparticles for grafting to a nanomaterial and/or a macromaterial. Addition of TTMSS to the metal nanoparticles so functionalized, with stirring under ambient air in the presence of a nanomaterial or a macromaterial forms new carbon-carbon linkages between the metal nanoparticles so functionalized and the nanomaterial or macromaterial provided.

In some embodiments of the present invention, the processes to functionalize metal nanoparticles are applied to functionalize metal surfaces for the purpose of coating such metal surfaces with nanomaterials. The methods of such processes to functionalize metal surfaces are identical to those to functionalize metal nanoparticles disclosed above, however, in all instances where metal nanoparticles serve as the substrate, a metal surface serves as the substrate instead.

The examples below illustrate specific embodiments of the invention.

EXAMPLES

The following general procedures were followed in the context of methods of the invention. MWCNTs (NC 7000 Thin Multiwall Carbon Nanotubes) synthesized via chemical vapor deposition with carbon purity 90%, average diameter 9.5 nm, and average length 1.5 microns were procured from Nanocyl S.A. (Sambreville, Belgium) and used as received. Plasma exfoliated graphene nanoplatelets (Grade 4, research) with thickness <4 nm and surface area >700 $m^2/g$ was purchased from Cheap Tubes Inc. (Brattleboro, USA) and used as received. All solvents were used as received from Sigma Aldrich (USA). All other chemicals were of reagent grade unless stated otherwise and used as received form Sigma Aldrich (USA).

Example 1

Facile Functionalization of CNTs for the Purposes of CNT Separation by Metallic Character and Attachment of Metallic Nanoparticles to CNTs To functionalize metallic CNTs with 1-bromo-3-chlorophenyl: add 20 g of MWCNTs to a 2 L reaction vessel with 750 ml of dioxane under stirring to provide the substrate suspended in dioxane. Next, add 3.17 g (0.010 moles) of 1-bromo-3-chloro-5-iodobenzene to the reaction mixture under stirring. Purge the reaction vessel of oxygen and carbon dioxide while stirring for 30 minutes. Add 2.98 (0.012 moles) of TTMSS to the reaction mixture. Expose the reaction vessel to ambient air and stir for 2 hours at room temperature. Quench reaction with flowing ambient air over reaction mixture to yield 1-bromo-3-chlorophenyl functionalized metallic CNTs.

To convert 1-bromo-3-chlorophenyl functionalized metallic CNTs to magnetite functionalized metallic CNTs with magnetic properties, add additional substrate to the same reaction vessel: add 10 g of magnetite nanoparticles to the reaction vessel under stirring. Purge the reaction vessel of oxygen and carbon dioxide while stirring for 30 minutes. Add additional TTMSS: add 2.98 (0.012 moles) of TTMSS to the reaction mixture. Expose the reaction vessel to ambient air and stir for 3 hours at room temperature. Quench reaction with flowing ambient air over reaction mixture to yield magnetite functionalized metallic CNTs.

To separate magnetite functionalized metallic CNTs from unreacted semi-conducting CNTs, transfer mixture to 1 L flask. Secure magnets to outside of flask and stir reaction mixture occasionally while under sonication for 30 minutes. Separate functionalized metallic CNTs attracted to magnets from unreacted semi-conducting CNTs. Immerse functionalized metallic CNTs in aqueous solution with sulfuric acid and mix for 10 minutes to dissolve iron oxide if so desired. Wash with copious amounts of DI water following acid treatment To convert functionalized metallic CNTs to gold nanoparticle-metallic CNT nanohybrids, continue reaction in same 2 L reaction vessel if acid treatment eschewed. Otherwise, add acid-treated functionalized metallic CNTs to a clean 2 L reaction vessel with 500 ml of dioxane. Purge the reaction vessel of oxygen and carbon dioxide while stirring for 30 minutes. Add 5.96 (0.024 moles) of TTMSS to the reaction. Expose the reaction vessel to ambient air and stir for 6 hours at room temperature. Quench reaction with flowing ambient air over reaction mixture. Wash reaction mixture thoroughly with copious amounts of water followed by isopropyl alcohol. Dry product under vacuum to yield a metallic CNT-gold nanoparticle nanohybrid Example 2

Facile Thiol Functionalization of Carbon Nanomaterials for the Purposes of Manufacturing a Nylon Compatible Ultra-Stable Silver Nanoparticle-Carbon Nanomaterial Nanohybrid To functionalize carbon nanomaterials with 4-bromophenyl, provide the substrate: add 20 g of MWCNTs and 5 g of graphene to a 2 L jacketed reaction vessel with 500 ml of dioxane. Add the functionalizing unit: 2.82 g (0.010 moles) of 1-bromo-4-iodobenzene to the reaction mixture under stirring. Purge the reaction vessel of oxygen and carbon dioxide while stirring for 30 minutes. Add 2.98 (0.012 moles) of TTMSS to the reaction mixture. Expose the reaction vessel to ambient air and stir for 2 hours at room temperature. Quench reaction with flowing ambient air over reaction mixture.

To convert 4-bromophenyl functionalized carbon nanomaterials to thiophenyl functionalized carbon nanomaterials, continue reaction adding 3.04 g (0.040 moles) of excess thiourea to the reaction vessel under stirring. Attach reflux condenser to reaction vessel. Heat reaction mixture to 93° Celsius and stir for 2 hours. Wash product with water, followed by ethanol to yield thiophenyl functionalized carbon nanomaterials.

To manufacture ultra-stable silver nanoparticle-carbon nanomaterial nanohybrids, continue reaction by adding thiophenyl functionalized carbon nanomaterials to a 2 L jacketed reaction vessel with 500 ml of ethanol and 500 ml of deionized water. Dissolve 89.03 g (0.44 moles) of silver methanesulfonate in reaction mixture under stirring for 30 minutes while cooling reaction vessel to 0° Celsius. Add 100 ml (0.44 moles) of 12 wt. % $NaBH_4$ in 14 M NaOH dropwise to reaction vessel under vigorous stirring and cooling. Ensure adequate ventilation and evacuate $H_2$ gas that may form in the reaction vessel as needed with a vacuum source. Stir for 1 hour at 0° Celsius. Dissolve 50 g (0.406 moles) of 4-aminothiophenol in ethanol and add dropwise to reaction vessel under cooling. Following aminthiophenol addition, stir reaction mixture for 2 hours while slowly raising reaction vessel temperature to room temperature. Add 1 g of sodium dodecylbenzene sulfonate to reaction vessel and stir reaction mixture for 30 minutes to disperse product. Wash reaction mixture thoroughly with copious amounts of water followed by isopropyl alcohol. Dry product under vacuum to yield 4-aminothiophenol capped ultra-stable metal nanoparticle-CNM nanohybrids.

Example 3

Facile Thiol Functionalization of Carbon Nanomaterials for the Purposes of Manufacturing a Water Compatible Ultra-Stable Silver Nanoparticle-Carbon Nanomaterial Nanohybrid Follow the methods of example 2, however, dissolve 62.6 g (0.406 moles) of 4-mercaptobenzoic acid in ethanol instead of 50 g (0.406 moles) of 4-aminothiophenol.

Example 4

Facile Functionalization of Tungsten Nanoparticles Under Ambient Air for the Purposes of Chemically Stabilizing, Thermally Stabilizing, and Priming Said Nanoparticles for Grafting to CNTs To functionalize tungsten nanoparticles in such a way as they may be chemically stabilized, thermally stabilized, and primed for grafting to a CNT, provide the substrate: add 10 g (0.0544 moles) of tungsten in the form of tungsten nanoparticles to 500 ml of cyclohexane in a 2 L reaction vessel. Add the bi-functional and sterically hindered functionalizing unit: add 12.44 g (0.040 moles) of 1-bromo-2, 6-dimetyl-4-iodobenzene to the reaction mixture under stirring. Purge the reaction vessel of oxygen and carbon dioxide. Add 5 g (0.020 moles) of TTMSS to the reaction mixture. Expose the reaction vessel to ambient air and stir for 2 hours at room temperature. Quench reaction with flowing ambient air over reaction mixture to yield 1-bromo-2,6-dimethylphenyl functionalized tungsten metal nanoparticles.

To graft 1-bromo-2,6-dimethylphenyl functionalized tungsten metal nanoparticles to CNTs, continue reaction in same reaction vessel, with 1-bromo-2,6-dimethylphenyl functionalized tungsten metal nanoparticles serving now as a functionalizing unit. Add additional substrate to the same reaction vessel: add 25 g of carbon nanotubes to the reaction vessel under stirring. Purge the reaction vessel of oxygen and carbon dioxide while stirring for 30 minutes. Add additional TTMSS: add 2.98 g (0.012 moles) of TTMSS to the reaction mixture. Expose the reaction vessel to ambient air and stir for 4 hours at room temperature. Quench reaction with flowing ambient air over reaction mixture to yield tungsten nanoparticle functionalized CNTs.

Example 5

Facile Functionalization of Tungsten Nanoparticles Under Ambient Air for the Purposes of Chemically Stabilizing, Thermally Stabilizing, and Priming Said Nanoparticles for Grafting from CNTs To functionalize tungsten nanoparticles in such a way as they may be chemically stabilized, thermally stabilized, and primed for grafting from a CNT, provide the substrate: add 10 g (0.0544 moles) of tungsten in the form of tungsten nanoparticles to 500 ml of cyclohexane in a 2 L reaction vessel. Add the mono-functional and sterically hindered functionalizing unit: add 9.28 g (0.040 moles) of 1-iodo-3, 5-dimetylbenzene to the reaction mixture under stirring. Purge the reaction vessel of oxygen and carbon dioxide. Add 5 g (0.20 moles) of TTMSS to the reaction mixture. Expose the reaction vessel to ambient air and stir for 2 hours at room temperature. Quench reaction with flowing ambient air over reaction mixture to yield 3,5-dimethylphenyl functionalized tungsten metal nanoparticles.

To provide functionalized CNTs from which 3,5-dimethylphenyl functionalized tungsten metal nanoparticles may graft from: provide the substrate: add 25 g of carbon nanotubes to a separate 2 L reaction vessel with 500 ml of cyclohexane under stirring. Add the functionalizing unit: add 2.83 g (0.010 moles) of 1-bromo-4-iodobenzene to the reaction mixture under stirring. Purge the reaction vessel of oxygen and carbon dioxide while stirring for 30 minutes. Add 2.98 g (0.012 moles) of TTMSS to the reaction mixture. Expose the reaction vessel to ambient air and stir for 2 hours at room temperature. Quench reaction with flowing ambient air over reaction mixture to yield 1-bromophenyl functionalized CNTs.

To graft 3,5-dimethylphenyl functionalized tungsten metal nanoparticles from 1-bromophenyl functionalized CNTs, add the functionalizing unit: add the mixture containing 1-bromophenyl functionalized CNTs to the reaction vessel containing the 3,5-dimethylphenyl functionalized tungsten metal nanoparticles. Purge the reaction vessel of oxygen and carbon dioxide while stirring for 30 minutes. Add additional TTMSS: 2.98 g (0.012 moles) of TTMSS to the reaction mixture. Expose the reaction vessel to ambient air and stir for 4 hours at room temperature. Quench reaction with flowing ambient air over reaction mixture to yield tungsten nanoparticle functionalized CNTs.

Example 6

Facile Functionalization of Titanium Nanoparticles Under an Inert-Environment for the Purposes of Chemically Stabilizing, Thermally Stabilizing, and Priming Said Nanoparticles for Grafting to CNTs To functionalize titanium nanoparticles in such a way as they may be chemically stabilized, thermally stabilized, and primed for grafting to a CNT, provide the substrate: add 5 g (0.1045 moles) of titanium in the form of titanium nanoparticles to 500 ml of cyclohexane in a 2 L reaction vessel under an inert atmosphere. Add the mono-functional diazonium salt functionalizing unit: add 4.60 g (0.017 moles) of 4-bromobenzenediazonium tetrafluoroborate to the reaction mixture under stirring. Add 5.07 g (0.0204 moles) of TTMSS to the reaction mixture. Stir the reaction mixture for 2 hours at room temperature. Quench reaction with flowing ambient air over reaction mixture to yield bromophenyl functionalized aluminum metal nanoparticles.

To graft bromophenyl functionalized aluminum metal nanoparticles to CNTs, continue reaction in same reaction vessel, with bromophenyl functionalized aluminum metal nanoparticles serving now as a functionalizing unit. Add additional substrate to the same reaction vessel: add 25 g of carbon nanotubes to the reaction vessel under stirring. Purge the reaction vessel of oxygen and carbon dioxide while stirring for 30 minutes. Add additional TTMSS: add 2.98 g (0.012 moles) of TTMSS to the reaction mixture. Expose the reaction vessel to ambient air and stir for 4 hours at room temperature. Quench reaction with flowing ambient air over reaction mixture to yield aluminum nanoparticle functionalized CNTs.

Example 7

Facile Functionalization of Aluminum Nanoparticles Under an Inert-Environment for the Purposes of Chemically Stabilizing, Thermally Stabilizing, and Priming Said Nanoparticles for Grafting from CNTs To functionalize aluminum nanoparticles in such a way as they may be chemically stabilized, thermally stabilized, and primed for grafting from a CNT, provide the substrate: add 10 g (0.37 moles) of aluminum in the form of aluminum nanoparticles to 500 ml of dioxane in a 2 L jacketed reaction vessel under an inert atmosphere. Add the mono-functional functionalizing unit: add 24.89 g (0.122 moles) of iodobenzene to the reaction mixture under stirring. Add 36.40 g (0.1464 moles) of TTMSS to the reaction mixture. Add the radical initiator: add 20.03 g (0.122 moles) of AIBN under stirring. Heat the reaction vessel to 80° Celsius and stir for 3 hours at 80° Celsius. Quench reaction with flowing ambient air over reaction mixture to yield phenyl functionalized aluminum metal nanoparticles.

To provide functionalized CNTs from which phenyl functionalized aluminum metal nanoparticles may graft from: provide the substrate: add 25 g of carbon nanotubes to a separate 2 L reaction vessel with 500 ml of dioxane under stirring. Add the functionalizing unit: add 2.83 g (0.010 moles) of 1-bromo-4-iodobenzene to the reaction mixture under stirring. Purge the reaction vessel of oxygen and carbon dioxide while stirring for 30 minutes. Add 2.98 g (0.012 moles) of TTMSS to the reaction mixture. Expose the reaction vessel to ambient air and stir for 2 hours at room temperature. Quench reaction with flowing ambient air over reaction mixture to yield 1-bromophenyl functionalized CNTs.

To graft phenyl functionalized aluminum metal nanoparticles from 1-bromophenyl functionalized CNTs, add the functionalizing unit: add the mixture containing 1-bromophenyl functionalized CNTs to the reaction vessel containing the phenyl functionalized aluminum metal nanoparticles. Purge the reaction vessel of oxygen and carbon dioxide while stirring for 30 minutes. Add additional TTMSS: 2.98 g (0.012 moles) of TTMSS to the reaction mixture. Expose the reaction vessel to ambient air and stir for 4 hours at room temperature. Quench reaction with flowing ambient air over reaction mixture to yield aluminum nanoparticle functionalized CNTs.

Example 8

Facile Functionalization of Polylactic Acid with Multi-Walled CNTs 280 grams of polylactic acid (PLA) (MW=200,000) was dissolved in 1 L dioxane or THF at 65° C. while stirring. To this mixture, 1 ml of 4-bromobutyryl chloride (0.008 mol) was added. The resulting mixture was stirred for an hour and cooled to 35° C. to provide the bromobutyrylated-PLA. Thereafter, multi-walled CNTs (about 6.7 wt % of PLA) was added under stirring. The resulting mixture was stirred for an hour at 400-800 rpm under nitrogen purge. TTMSS was the added under nitrogen purge and stirring. The reaction mixture was then exposed to air and stir in air for 3 hours to provide a crude product. At the completion of the reaction, the CNTs were seen to have fully dispersed in PLA as they are covalently bound to PLA.

The final crude product was precipitated out by adding heptane. The solvents (including dioxane or THF, as well heptane) were removed. The final functionalized PLA was collected as conductive powder.

Example 9

Facile Functionalization of Polylactic Acid with Capped Ultra-Stable Silver Nanoparticles To a sonicating flask, 12 g MWCNTs (or graphene) (1 mol), 1-chloro-3-iodopropane (CIP) (1.074 ml, 0.01 mol) were mixed with 800 ml dioxane. The mixture was alternately sonicated at mid power for 5 minutes and stirred for 5 minutes for a total of 30 minutes or until no stirring could be effected.

The sonicated mixture was then transferred to a reactor and purged with nitrogen under stirring. TTMSS was added under nitrogen and stirring. The reaction was allowed to run for 3 hours while exposed to air to produce the chloropropyl-functionalized CNTs. A solution of 7.6 g thiourea in 800 ml of water was then added and the mixture was stirred with a condenser at 90° C. for 3 hours to effect the substitution reaction of chloro for thiol. The crude product was filtered and rinsed with water (see also FIG. 3A)

The thiol-functionalized CNTs (13 g, 0.01 mol thiol) were sonicated in water with NaOH and transferred to a reactor. Silver nitrate (75 g, 0.44 mol) in 250 ml DI water was added dropsies under stirring. The reaction was purged with nitrogen and stirred for no more than 1 hour before reducing the temperature to less than 4° C. One fifth of a solution including 50 g 3-ABBA in 250 ml water and 1 mol of NaOH was added to the thiol-functionalized CNTs and silver nitrate reaction dropwise over 10 minutes. A reducing solution of 100 g ascorbic acid in 250 ml DI water and 1 mol of NaOH was prepared (resulting in a sodium ascorbate solution). One fourth of the reducing solution was first added over half of an hour. Thereafter, the remainders of the 3-ABA solution and the reducing solution were added dropwise under stirring at <4° C. over 1 hour at equivalent rate such that sodium ascorbate and 3-ABA completely finish at nearly the same time. The resulting produce was washed with water three times and ethanol three times and centrifuged, dried under vacuum and stirring for 8 hours. (See also FIG. 4B)

50 g bromobutyrylated pLA was dissolved in THF in a 2 L reactor. Thereafter, 1 g of sodium carbonate or TBA carbonate was added and stirred for 20 minutes. 12 g of 3-ABA capped silver nanoparticle functionalized CNTs was added and stirred for 40 minutes Thereafter, 2 g of TBAI (quaternary ammonium iodide) was added and stirred for 2 hours to produce the PLA-composite by coupling the bromobutyrylated PLA with the 3-ABAs of the capped silver nanoparticles. See also FIG. 4C and FIG. 4D.

Although FIG. 4D shows only one coupling reaction, it should be understood that multiple coupling reactions can take place for bromobutyrylated PLA to couple to more or all of the 3-ABA molecules on the silver nanoparticles.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A process of functionalizing a substrate, comprising:
providing a substrate having a surface;
providing a reaction mixture by combining with the substrate:
(a) a functionalizing unit represented by Fn-$(X)_m$, wherein Fn is an organic moiety, X is, at each occurrence, the same or different and independently halogen, acyl halide, isocyanide, thionoester, xanthate, selenide, isocyanate, thiocyanate, sulfide, triflate, selenocyanide, or a Barton ester covalently connected to a respective carbon atom of Fn, and m is an integer ≥1;
(b) tris(trimethylsilyl)silane; and
(c) a radical initiator; and
allowing the reaction mixture to react for a sufficient period of time to provide a surface-functionalized substrate comprising one or more Fn covalently attached to the surface of the substrate, wherein the substrate includes a plurality of nanoparticles or microparticles.

2. The process of claim 1 wherein the substrate is silicon, a carbon allotrope, polymers, metal, metal-plated surfaces, or complex fluids.

3. The process of claim 1 wherein the nanoparticles or microparticles are carbon nanotubes, particles of graphene, buckyballs, carbyne, nano-diamonds, titanium dioxide, magnetite, metal, semiconductor or metal oxide.

4. The process of claim 1 wherein X is independently at each occurrence halogen, acyl halide, isocyanide, thionoester, xanthate, selenide, isocyanate, thiocyanate, sulfide, triflate, selenocyanide, or a Barton ester; and Fn is aryl, alkyl, alkenyl, alkynyl, cycloalkyl, cycloalkenyl, heterocyclyl, heteroaryl, or a combination thereof.

5. The process of claim 1 wherein the functionalizing unit is 3-chloro-1-iodopropane, 2-bromo-chloroethane, 1-bromopropionic acid, 1,4-diiodo-2,5-dimethylbenzene, 1,4-dibromo-2,5-dimethylbenzene, 1-bromo-2,6-dimethyl-4-iodobenzene, 1-bromo-2,5-dimethyl-iodobenzene, 1,4-diiodo-2,3,5,6-tetramethylbenzene, 1,4-dibromo-2,3,5,6-tetramethylbenzene, 3,5-diiodo-1-chlorobenzene, 1,3-dibromo-5-chlorobenzene, 1,3-diiodo-5-fluorobenzene, 1,3-dibromo-5-fluorobenzene, 1,4-diiodotetrachlorobenzene, 1,4-dibromotetrachlorobenzene, 1,4-diiodotetrafluorobenzene, and 1,4-dibromotetrafluorobenzene.

6. The process of claim 1 wherein the functionalizing unit comprises a polymer.

7. The process of claim 6 wherein the polymer is polylactic acid, polyamide, polyacrylic acids, acrylate, or polycarbonate.

8. The process of claim 1 wherein the radical initiator is oxygen and the reacting step comprises exposing the reaction mixture to air at ambient temperature.

9. A process for forming a composite material, comprising:
providing a first substrate;
providing a first reaction mixture by combining with the first substrate:
(a) a functionalizing unit represented by Fn-(X)m, wherein Fn is an organic moiety, X is, at each occurrence, the same or different and independently halogen, acyl halide, isocyanide, thionoester, xanthate, selenide, isocyanate, thiocyanate, sulfide, triflate, selenocyanide, or a Barton ester covalently connected to a respective carbon atom of Fn, and m is an integer ≥2;
(b) tris(trimethylsilyl)silane; and
(c) a radical initiator; and
allowing the first reaction mixture to react for a sufficient period of time to provide a functionalized first substrate comprising one or more Fn covalently attached to the surface of the first substrate, wherein the covalently attached Fn comprises at least one X group;
combining the functionalized first substrate with a second substrate with tris(trimethylsilyl)silane and a radical initiator to form a second reaction mixture; and
allowing the second reaction mixture to react for a sufficient period of time to provide a functionalized second substrate covalently bonded to the first substrate via Fn.

10. The process of claim 9 wherein the functionalized second substrate comprises a remaining X group on Fn, and the process further comprises:
combining the functionalized second substrate with a third substrate with tris(trimethylsilyl)silane and a radical initiator to form a third reaction mixture; and
allowing the third reaction mixture to react for a sufficient period of time to provide a functionalized third substrate covalently bonded to the first substrate and the second substrate via Fn.

11. The process of claim 9 wherein the nanoparticles are carbon nanotubes, particles of graphene, buckyballs, carbyne, nano-diamonds, titanium dioxide, magnetite, metal, semiconductor or metal oxide.

12. The process of claim 9 wherein X is independently at each occurrence halogen, acyl halide, isocyanide, thionoester, xanthate, selenide, isocyanate, thiocyanate, sulfide, triflate, selenocyanide, or a Barton ester, and wherein Fn is aryl, alkyl, alkenyl, alkynyl, cycloalkyl, cycloalkenyl, heterocyclyl, heteroaryl, or a combination thereof.

13. The process of claim 9 wherein the functionalizing unit is 1,4-diiodo-2,5-dimethylbenzene, 3-chloro-1-iodopropane, 2-bromo-chloroethane, 1-bromopropionic acid, 1,4-dibromo-2,5-dimethylbenzene, 1-bromo-2,6-dimethyl-4-iodobenzene, 1-bromo-2,5-dimethyl-iodobenzene, 1,4-diiodo-2,3,5,6-tetramethylbenzene, 1,4-dibromo-2,3,5,6- tetramethylbenzene, 3,5-diiodo-1-chlorobenzene, 1,3-dibromo-5-chlorobenzene, 1,3-diiodo-5-fluorobenzene, 1,3-dibromo-5-fluorobenzene, 1,4-diiodotetrachlorobenzene, 1,4-dibromotetrachlorobenzene, 1,4-diiodotetrafluorobenzene, and 1,4-dibromotetrafluorobenzene.

14. The process of claim 9 wherein the functionalizing unit comprises a polymer.

15. The process of claim 14 wherein the polymer is polylactic acid, polyamide, polyacrylic acids, acrylate, or polycarbonate.

16. A process for forming a composite material, comprising:
    providing a premix mixture of a first substrate and a second substrate;
    providing a reaction mixture by combining the first and second substrate with:
    (a) a functionalizing unit represented by Fn-(X)m, wherein Fn is an organic moiety, X is, at each occurrence, the same or different and independently halogen, acyl halide, isocyanide, thionoester, xanthate, selenide, isocyanate, thiocyanate, sulfide, triflate, selenocyanide, or a Barton ester covalently connected to a respective carbon atom of Fn, and m is an integer ≥2; and
    (b) tris(trimethylsilyl)silane; and
    exposing the reaction to a radical initiator for a sufficient period of time to form covalent bonds between the first substrate and second substrate via Fn.

17. The process of claim 16 wherein the functionalizing unit and TTMSS are combined simultaneously with the premix mixture.

18. The process of claim 16 wherein first and second nanoparticles are independently carbon nanotubes, particles of graphene, buckyballs, carbyne, nano-diamonds, titanium dioxide, magnetite, metal, semiconductor or metal oxide.

* * * * *